(12) United States Patent
Miyoshi

(10) Patent No.: US 7,541,809 B2
(45) Date of Patent: Jun. 2, 2009

(54) MAGNETIC RESONANCE IMAGING APPARATUS

(75) Inventor: Mitsuharu Miyoshi, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 11/961,811

(22) Filed: Dec. 20, 2007

(65) Prior Publication Data

US 2008/0150530 A1 Jun. 26, 2008

(30) Foreign Application Priority Data

Dec. 22, 2006 (JP) ............................. 2006-346117

(51) Int. Cl.
*G01V 3/00* (2006.01)
(52) U.S. Cl. ...................................... 324/309; 324/306
(58) Field of Classification Search ................ 324/309, 324/307, 306
See application file for complete search history.

(56) References Cited

U.S. PATENT DOCUMENTS

| 5,281,916 A | * | 1/1994 | Hinks et al. .................. 324/309 |
| 5,285,158 A | | 2/1994 | Mistretta et al. |
| 5,548,216 A | * | 8/1996 | Dumoulin et al. ........... 324/309 |

(Continued)

FOREIGN PATENT DOCUMENTS

JP 2000-005144 1/2000

(Continued)

OTHER PUBLICATIONS

Nana et al., Ex vivo MR diffusion anisotropy measurement for the evaluation of gastric tissue fiber directions using 3D Turbo Steam sequence, Proceedings, International Society for Magnetic Resonance in Medicine, Jan. 1, 2006, p. 2227.

(Continued)

*Primary Examiner*—Louis M Arana
(74) *Attorney, Agent, or Firm*—Armstrong Teasdale LLP

(57) ABSTRACT

A magnetic resonance imaging apparatus which executes an imaging sequence for obtaining, as imaging data, magnetic resonance signals each generated from a spin excited at a subject within a static magnetic field space and produces an image about the subject, based on the imaging data obtained by the execution of the imaging sequence, includes a scan section which executes the imaging sequence and executes, before the execution of the imaging sequence, a preparation sequence for transmitting preparation pulses to the subject in such a manner that signal intensities of the magnetic resonance signals differ according to the velocities of spins moved in the subject, wherein the scan section sequentially transmits, as the preparation pulses, a first RF pulse, a second RF pulse, a third RF pulse and a fourth RF pulse respectively to the subject, wherein the scan section transmits a first crusher gradient pulse constituted of a pair of gradient pulses to the subject in such a manner that a point of time at which an RF pulse is transmitted as the second RF pulse is interposed at a time base, wherein the scan section transmits a second crusher gradient pulse constituted of a pair of gradient pulses to the subject in such a manner that a point of time at which an RF pulse is transmitted as the third RF pulse is interposed at the time base, and wherein the scan section transmits a killer gradient pulse to the subject after the transmission of the fourth RF pulse.

20 Claims, 16 Drawing Sheets

U.S. PATENT DOCUMENTS

| | | | |
|---|---|---|---|
| 5,729,139 A * | 3/1998 | Goto | 324/309 |
| 5,786,692 A * | 7/1998 | Maier et al. | 324/307 |
| 5,899,858 A | 5/1999 | Muthupillai et al. | |
| 6,008,647 A * | 12/1999 | Zhou et al. | 324/309 |
| 6,078,176 A * | 6/2000 | McKinnon | 324/309 |
| 6,320,377 B1 | 11/2001 | Miyazaki et al. | |
| 6,353,752 B1 | 3/2002 | Madore et al. | |
| 6,438,404 B1 | 8/2002 | Van Den Brink et al. | |
| 6,479,995 B1 | 11/2002 | Ogino | |
| 6,614,225 B1 | 9/2003 | Feinberg | |
| 6,782,286 B2 | 8/2004 | Miyazaki | |
| 6,801,800 B2 | 10/2004 | Miyazaki | |
| 7,058,440 B2 | 6/2006 | Heuscher et al. | |
| 7,141,972 B2 | 11/2006 | Avram et al. | |
| 7,176,681 B2 | 2/2007 | Zombo | |
| 2004/0059213 A1 | 3/2004 | Kassai et al. | |
| 2004/0162483 A1 | 8/2004 | Kimura | |

FOREIGN PATENT DOCUMENTS

| | | |
|---|---|---|
| JP | 2002-200054 | 7/2002 |

OTHER PUBLICATIONS

Yongbi et al., A Modified Sub-Second Fast-Steam Sequence Incorporating Bipolar Gradients for in Vivo Diffusion Imaging, Magnetic Resonance in Medicine, Academic Press, Jun. 1, 1996, pp. 911-916.

International Search Report, NL1034839, dated Dec. 16, 2008, pp. 12.

* cited by examiner

MAGNETIC RESONANCE IMAGING APPARATUS

CROSS REFERENCE TO RELATED APPLICATIONS

This application claims the benefit of Japanese Patent Application No. 2006-346117 filed Dec. 22, 2006.

BACKGROUND OF THE INVENTION

The present invention relates to a magnetic resonance imaging apparatus, and to a magnetic resonance imaging apparatus which executes an imaging sequence for obtaining magnetic resonance signals generated by transmitting RF pulses to a subject SU in a static magnetic field space and transmitting gradient pulses to the subject to which the RF pulses are transmitted, as imaging data, and thereby generates images about the subject on the basis of the imaging data obtained by the execution of the imaging sequence.

A magnetic resonance imaging (MRI) apparatus is frequently made available for a medical use in particular as an apparatus for photographing an image about a tomographic plane of a subject, using a nuclear magnetic resonance (NMR) phenomenon.

In the magnetic resonance imaging apparatus, a subject is accommodated in an imaging space formed with a static magnetic field thereby to arrange spins of proton in the subject in the direction in which the static magnetic field is formed, and a magnetization vector thereof is produced. A scan for applying an RF pulse having a resonant frequency to generate a nuclear magnetic resonance phenomenon, thereby flipping the spins and, after the magnetization vector of the proton is changed, receiving magnetic resonance (MR) signals produced when the spins are arranged along the static magnetic field direction and the proton is returned to the original state of magnetization vector, is executed as an imaging sequence. The magnetic resonance signals obtained by execution of the imaging sequence are set as imaging data, and images such as a slice image and the like about the subject are generated.

In the present magnetic resonance imaging apparatus, blood photography called "MRA (MR angiography)" is carried out to represent or project flows of blood and the like that flow through the blood vessels. There is known an imaging method using a time of flight (TOF) effect, a phase contrast (PC) effect or the like for MRA. FBI (Fresh Blood Imaging) has been proposed as an imaging method using no contrast agent (refer to, for example, patent documents 1 and 2).

Patent Document 1. Japanese Unexamined Patent Publication No. 2000-5144.

Patent Document 2. Japanese Unexamined Patent Publication No. 2002-200054.

In the FBI method, an imaging sequence is carried out during cardiac diastole and cardiac systole to produce images about a subject. An MRA image related to the subject is obtained based on the value of a difference between these images. This method applies a flow boid or void of an FSE (Fast Spin Echo) method.

Described specifically, the imaging sequence is carried out during cardiac diastole to produce a first image. For instance, crusher gradient pulses are transmitted in a slice direction without transmitting gradient pulses for flow compensation in a read direction and without transmitting the crusher gradient pulses in a warp direction, thereby carrying out a scan to produce a first image.

The imaging sequence is executed during cardiac systole to produce a second image. For instance, a scan is executed by transmitting crusher gradient pulses in read, warp and slice directions before transmission of read gradient pulses for reading magnetic resonance signals. Thus, flow voids are produced in the respective axial directions to generate a second image.

Thereafter, an MRA image about the subject is obtained based on the value of difference between the first and second images. Since the blood-flow velocity of an artery is fast during cardiac systole here, a signal intensity from the artery becomes low, whereas since the blood-flow velocity of the artery is slow during cardiac diastole, a signal intensity from the artery becomes high. Therefore, the MRA image generated based on the above-described value of difference becomes high in contrast. Described specifically, only a portion in which a flow void has occurred in the second image is projected.

Since, however, the above method encounters difficulties in predicting the degree of occurrence of flow voids, the MRA image might not be produced with sufficient high contrast. It was thus difficult to obtain suitable image quality.

Since no flow void occurs in a flow lying in such a direction that a synthesis in the read and warp directions becomes zero, the flow might not be projected suitably. Therefore, the above method encountered difficulties in producing an MRA image with high accuracy.

Since the MRA image is generated based on the value of difference between the first and second images in the above method, the signal intensity becomes not greater than the first image and noise reaches $\sqrt{2}$ times. Therefore, there was a case in which obtaining sufficient image quality was difficult because the MRA image became $1/\sqrt{2}$ or less in S/N ratio with respect to the first image.

There was a case in which since the acquisition of magnetic resonance signals was limited to the FSE method, general versatility was insufficient in the above method.

Therefore, the above method encountered difficulties in enhancing diagnostic efficiency because general versatility was poor and image quality was deteriorated.

SUMMARY OF THE INVENTION

It is desirable that the problems described previously are solved.

In one aspect of the invention, a magnetic resonance imaging apparatus which executes an imaging sequence for obtaining, as imaging data, magnetic resonance signals each generated from a spin excited at a subject within a static magnetic field space and produces an image about the subject, based on the imaging data obtained by the execution of the imaging sequence, includes a scan section which executes the imaging sequence and executes, before the execution of the imaging sequence, a preparation sequence for transmitting preparation pulses to the subject in such a manner that signal intensities of the magnetic resonance signals differ according to the velocities of spins moved in the subject. The scan section sequentially transmits, as the preparation pulses, a first RF pulse, a second RF pulse, a third RF pulse and a fourth RF pulse respectively to the subject. The scan section transmits a first crusher gradient pulse constituted of a pair of gradient pulses to the subject in such a manner that a point of time at which an RF pulse is transmitted as the second RF pulse is interposed at a time base. The scan section transmits a second crusher gradient pulse constituted of a pair of gradient pulses to the subject in such a manner that a point of time at which an RF pulse is transmitted as the third RF pulse is interposed at the time base. The scan section transmits a killer gradient pulse to the subject after the transmission of the fourth RF pulse.

Preferably, the scan section transmits the first RF pulse and the fourth RF pulse in such a manner that their phases are the same, the absolute values of their flip angles are the same and their signs are opposite to each other. Preferably, the scan section transmits the first RF pulse and the fourth RF pulse in such a manner that the absolute values of the flip angles assume 90°.

Preferably, the scan section transmits the second RF pulse and the third RF pulse in such a manner that the phases thereof are orthogonal to the phases of the first RF pulse and the fourth RF pulse.

Preferably, the scan section transmits the second RF pulse and the third RF pulse in such a manner that the absolute values of the flip angles are identical to each other.

Preferably, the scan section sequentially transmits the first RF pulse, the second RF pulse, the third RF pulse and the fourth RF pulse respectively to the subject in such a manner that a second time interval defined between a central point of time at which the second RF pulse is transmitted, and a central point of time at which the third RF pulse is transmitted, is twice as much as a first time interval defined between a central point of time at which the first RF pulse is transmitted and a central point of time at which the second RF pulse is transmitted, and a third time interval defined between a central point of time at which the third RF pulse is transmitted and a central point of time at which the fourth RF pulse is transmitted, is identical to the first time interval.

Preferably, the scan section transmits a plurality of RF pulses including a 180° pulse as the second RF pulse, and transmits a plurality of RF pulses including the 180° pulse as the third RF pulse.

Preferably, the scan section transmits the RF pulses respectively transmitted as the second RF pulse and the third RF pulse in such a manner that their phases are the same, the absolute values of their flip angles are the same and their signs are opposite to each other.

Preferably, the scan section sequentially transmits α° pulses other than the 180° pulse, and 180° pulses as the RF pulses respectively transmitted as the second RF pulse and the third RF pulse.

Preferably, the scan section transmits the first crusher gradient pulse and the second crusher gradient pulse respectively in such a manner that a gradient pulse transmitted between the first RF pulse and the second RF pulse and a gradient pulse transmitted between the third RF pulse and the fourth RF pulse, of a plurality of gradient pulses respectively transmitted as the first crusher gradient pulse and the second crusher gradient pulse, are respectively set to the same first time integration value with respect to each other, and the whole time integration value of gradient pulses respectively transmitted as the second RF pulse and the third RF pulse between a plurality of RF pulses is set to a second time integration value equal to twice the first time integration value.

Preferably, the scan section transmits, as the preparation pulses, velocity encode gradient pulses for shifting the phases of moving spins in a different way according to the velocities of the moving spins in the spins of the subject.

Preferably, the scan section transmits the velocity encode gradient pulses such that they are opposite to each other in polarity at the time base about central points of time at which the velocity encode gradient pulses are transmitted.

Preferably, there is provided an image generation unit which produces an image about the subject, based on the imaging data, and the scan section acquires a magnetic resonance signal produced by executing the imaging sequence after the preparation sequence has been executed as a first preparation pulse sequence, as first imaging data, and the scan section acquires, as second imaging data, a magnetic resonance signal produced by executing the imaging sequence after a second preparation pulse sequence for transmitting the same preparation pulses as in the first preparation sequence is executed as the preparation sequence, except that the crusher gradient pulses and the velocity encode gradient pulse are not transmitted and the flip angles of the second RF pulse and the third RF pulse are different from each other, and the image generation unit generates a first image, based on the first imaging data and generates a second image, based on the second imaging data, and thereafter generates, as the image, a difference image by carrying out a difference process between the first and second images.

Preferably, the scan section transmits, as the preparation pulse, a killer gradient pulse for generating a gradient magnetic field that causes transverse magnetization of each spin to disappear at the subject, before the transmission of the first RF pulse.

Preferably, the scan section transmits the first RF pulse, the second RF pulse, the third RF pulse and the fourth RF pulse as rectangular pulses respectively.

Preferably, the scan section performs the preparation sequence during cardiac systole at cardiac motion of the subject, and performs the imaging sequence during cardiac diastole at the cardiac motion.

According to the invention, there can be provided a magnetic resonance imaging apparatus high in general versatility and capable of improving image quality.

Further objects and advantages of the present invention will be apparent from the following description of the preferred embodiments of the invention as illustrated in the accompanying drawings.

DETAILED DESCRIPTION OF THE INVENTION

First embodiment. A first embodiment according to the invention will be explained.

Apparatus Construction.

Figure 1:
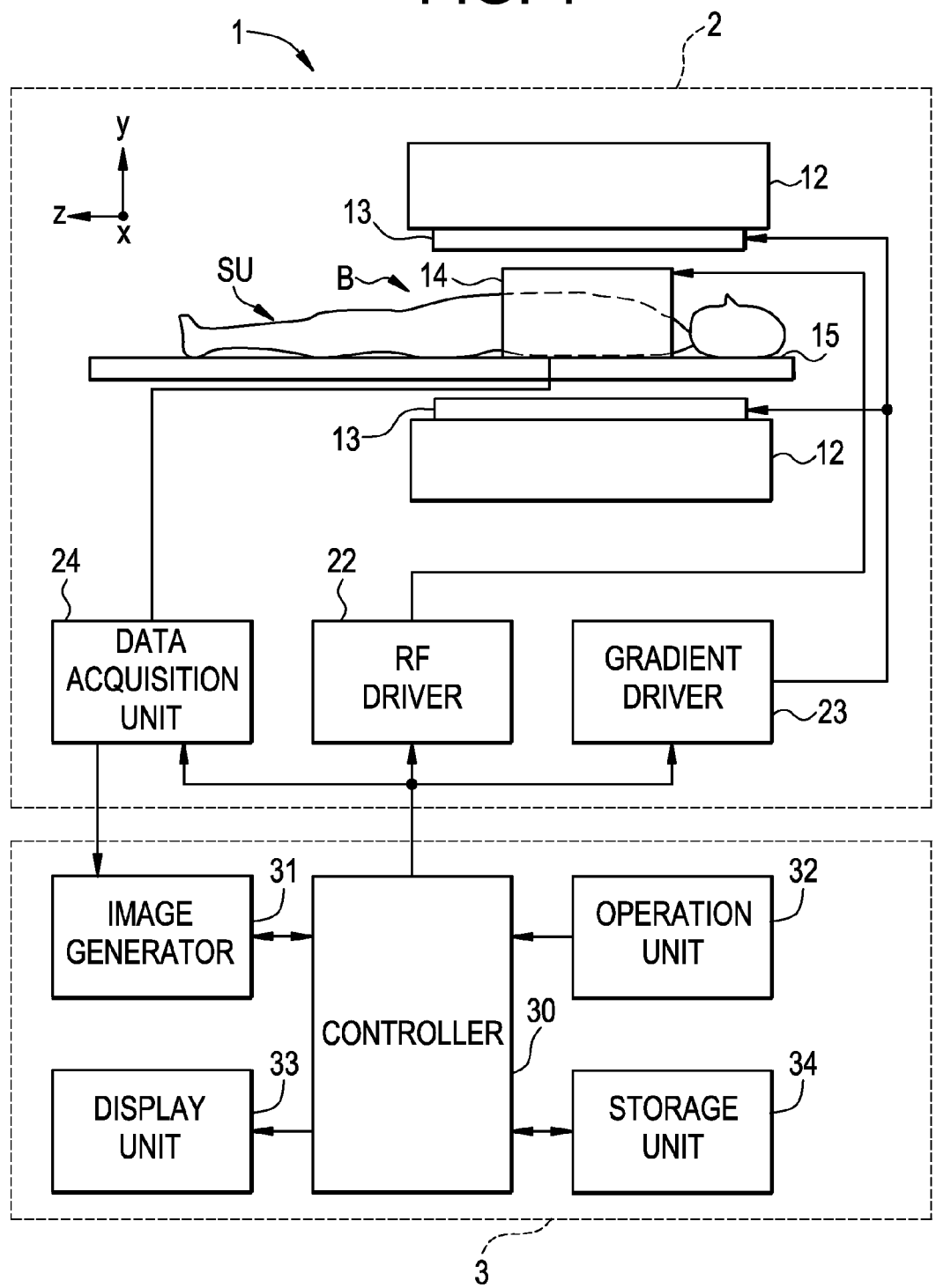
FIG. 1 is a configurational diagram showing a construction of a magnetic resonance imaging apparatus 1 illustrative of a first embodiment according to the invention.

FIG. 1 is a configurational diagram showing a construction of a magnetic resonance imaging apparatus 1 illustrative of the first embodiment according to the invention.

As shown in FIG. 1, the magnetic resonance imaging apparatus 1 of the present embodiment has a scan section 2 and an operation console section 3. The magnetic resonance imaging apparatus 1 executes an imaging sequence for obtaining a magnetic resonance signal generated from each of spins excited at a subject in an imaging space formed with a static magnetic field, as imaging data and generates a subject's image on the basis of the imaging data obtained by the execution of the imaging sequence.

In the present embodiment, an imaging sequence for holding or accommodating a subject containing spins corresponding to a first spin held in a stationary state at a first velocity corresponding to a velocity of 0 and a second spin held in a moving state, which moves at a second velocity different from the first velocity, in its corresponding imaging space B formed with a static magnetic field, and transmitting each RF pulse to the subject accommodated in the imaging space B, thereby exciting the spins to obtain magnetic resonance signals generated from the excited spins as imaging data is executed. Thereafter, images about the subject are generated based on the imaging data obtained by the execution of the imaging sequence.

The scan section 2 will be explained.

As shown in FIG. 1, the scan section 2 has a static magnetic field magnet unit 12, a gradient coil unit 13, an RF coil unit or part 14, a cradle 15, an RF driver 22, a gradient driver 23 and a data acquisition unit 24. As described above, the scan section 2 carried out an imaging sequence IS for transmitting RF pulses to the subject SU so as to excite the spins in the subject SU within the imaging space B formed with the static magnetic field and transmitting gradient pulses to the subject SU to which the RF pulses have been transmitted, thereby obtaining magnetic resonance signals generated at the subject SU as imaging data. Along with the execution of the imaging sequence IS, the scan section 2 executes a preparation sequence PS for transmitting preparation pulses to the subject in such a manner that the intensities of the magnetic resonance signals differ according to the velocities of the spins moved at the subject, prior to the execution of the imaging sequence IS. Described specifically, the preparation sequence for transmitting the preparation pulses to the subject in such a manner that, for example, a magnetic resonance signal generated from a first spin held in a stationary state and a magnetic resonance signal generated from a second spin held in a moving state are different from each other in signal intensity, is carried out prior to the execution of the imaging sequence.

Although the details thereof will be described later, the scan section 2 sequentially transmits a first RF pulse, a second RF pulse, a third RF pulse and a fourth RF pulse, respectively, to the subject as the preparation pulses in the preparation sequence PS. Along with it, crusher gradient pulses are transmitted to the subject in such a manner that the times when the second and third RF pulses are respectively transmitted are interposed between time bases. Here, a first crusher gradient pulse constituted of a pair of gradient pulses is transmitted to the subject in such a manner the time when an RF pulse is transmitted as the second RF pulse is interposed between the time bases, and a second crusher gradient pulse constituted of a pair of gradient pulses is transmitted to the subject in such a manner that the time when an RF pulse is transmitted to the subject as the third RF pulse is interposed between the time bases. After transmission of the fourth RF pulse and transmission of the crusher gradient pulses, killer gradient pulses are transmitted to the subject.

Thereafter, the scan section 2 executes an imaging sequence IS by an SSFP (Steady State Free Precession) type imaging method called, for example, an FIESTA, True FISP, Balanced TFE or the like.

Respective constituent elements of the scan section 2 will be explained sequentially.

The static magnetic field magnet unit 12 is a horizontal magnetic filed type, for example. A superconductive magnet (not shown) forms a static magnetic field so as to extend along the direction (z direction) of a body axis of the subject SU placed in the imaging space B in which the subject SU is accommodated or held. Incidentally, the static magnetic field magnet unit 12 may be a vertical magnetic field type in addition to the horizontal magnetic field type. A pair of permanent magnets may form a static magnetic field along their faced directions.

The gradient coil unit 13 forms a gradient magnetic field in the imaging space B formed with the static magnetic field and applies or adds spatial position information to the magnetic resonance signal received by the RF coil unit 14. Here, the gradient coil unit 13 comprises three systems set so as to correspond to three-axis directions of a z direction, an x direction and a y direction orthogonal to one another, which extend along the direction of the static magnetic field. These transmit gradient pulses in a frequency encode direction, a phase encode direction and a slice selection direction respectively according to set imaging conditions thereby to form gradient magnetic fields. Described specifically, the gradient coil unit 13 applies the gradient magnetic field in the slice selection direction of the subject SU and selects a slice of the subject SU excited by transmission of the RF pulse by the RF coil unit 14. The gradient coil unit 13 applies the gradient magnetic field in the phase encode direction of the subject SU and phase-encodes a magnetic resonance signal from the slice excited by the RF pulse. And the gradient coil unit 13 applies the gradient magnetic field in the frequency encode direction of the subject SU and frequency-encodes the magnetic resonance signal from the slice excited by the RF pulse.

As shown in FIG. 1, the RF coil unit 14 is disposed so as to surround the subject SU. The RF coil unit 14 transmits the RF pulse corresponding to an electromagnetic wave to the subject SU within the imaging space B formed with the static magnetic field by the static magnetic field magnet unit 12 to form a high frequency magnetic field, thereby exciting the spins of proton in an imaging area of the subject SU. The RF coil unit 14 receives an electromagnetic wave generated from the excited proton in the subject SU as a magnetic resonance signal.

The cradle 15 has a pedestal or table on which the subject SU is placed. A cradle section 26 is moved between the inside and outside of the imaging space B, based on a control signal supplied from a controller 30.

The RF driver 22 drives the RF coil unit 14 to transmit an RF pulse to within the imaging space B, thereby forming a high frequency magnetic field. The RF driver 22 modulates a signal sent from an RF oscillator to a signal having predetermined timing and predetermined envelope using a gate modulator on the basis of the control signal outputted from the controller 30. Thereafter, the RF driver 22 allows an RF power amplifier to amplify the signal modulated by the gate modulator and outputs the same to the RF coil unit 14, and allows the RF coil unit 14 to transmit the RF pulse.

The gradient driver 23 applies a gradient pulse to the gradient coil unit 13 based on the control signal outputted from the controller 30 to drive the gradient coil unit 13, thereby to generate a gradient magnetic field within the imaging space B formed with the static magnetic field. The gradient driver 23 has a three-system drive circuit (not shown) in association with the three-system gradient coil unit 13.

The data acquisition unit 24 acquires each magnetic resonance signal received by the RF coil unit 14 based on the control signal outputted from the controller 30. Here, the data acquisition unit 24 phase-detects the magnetic resonance signal received by the RF coil unit 14 using a phase detector with the output of the RF oscillator of the RF driver 22 as a reference signal. Thereafter, the data acquisition unit 24 converts the magnetic resonance signal corresponding to the analog signal into a digital signal by using an A/D converter and outputs it therefrom.

The operation console section 3 will be explained.

As shown in FIG. 1, the operation console section 3 has a controller 30, an image generator 31, an operation unit 32, a display or display unit 33 and a storage unit 34.

Respective constituent elements of the operation console section 3 will be described sequentially.

The controller 30 has a computer and a memory that stores programs which allow the computer to execute predetermined data processing, and controls respective parts. Here, the controller 30 inputs operation data sent from the operation unit 32 and outputs the control signal to the RF driver 22, gradient driver 23 and data acquisition unit 24 respectively, based on the operation data inputted from the operation unit 32, thereby executing a predetermined scan. Along with it, the controller 30 outputs control signals to the image generator 31, display unit 33 and storage unit 34 to perform control on the respective parts.

The image generator 31 has a computer and a memory that stores programs which execute predetermined data processing using the computer. The image generator 31 executes data processing, based on the control signal supplied from the controller 30 to generate each image. Here, the image generator 31 uses the magnetic resonance signal obtained by executing a scan by the scan section 2 as raw data and reconstructs images about the subject SU. Then, the image generator 31 outputs each generated image to the display unit 33.

The operation unit 32 is constituted of an operation device such as a keyboard, a pointing device or the like. The operation unit 32 inputs operation data from an operator and outputs the same to the controller 30.

The display unit 33 is constituted of a display device such as a CRT and displays each image on its display screen, based on the control signal outputted from the controller 30. For example, the display unit 33 displays images about input items to which the operation data are inputted to the operation unit 32 by the operator, on the display screen in plural form. Further, the display unit 33 receives data about each image of the subject SU generated based on the magnetic resonance signal from the subject SU from the image generator 31 and displays the image on the display screen.

The storage unit 34 comprises a memory and stores various data therein. In the storage unit 34, the stored data are accessed by the controller 30 as needed.

Operation. Operation taken upon photographing the subject SU will be explained below using the magnetic resonance imaging apparatus 1 showing the above embodiment according to the invention.

Figure 2:
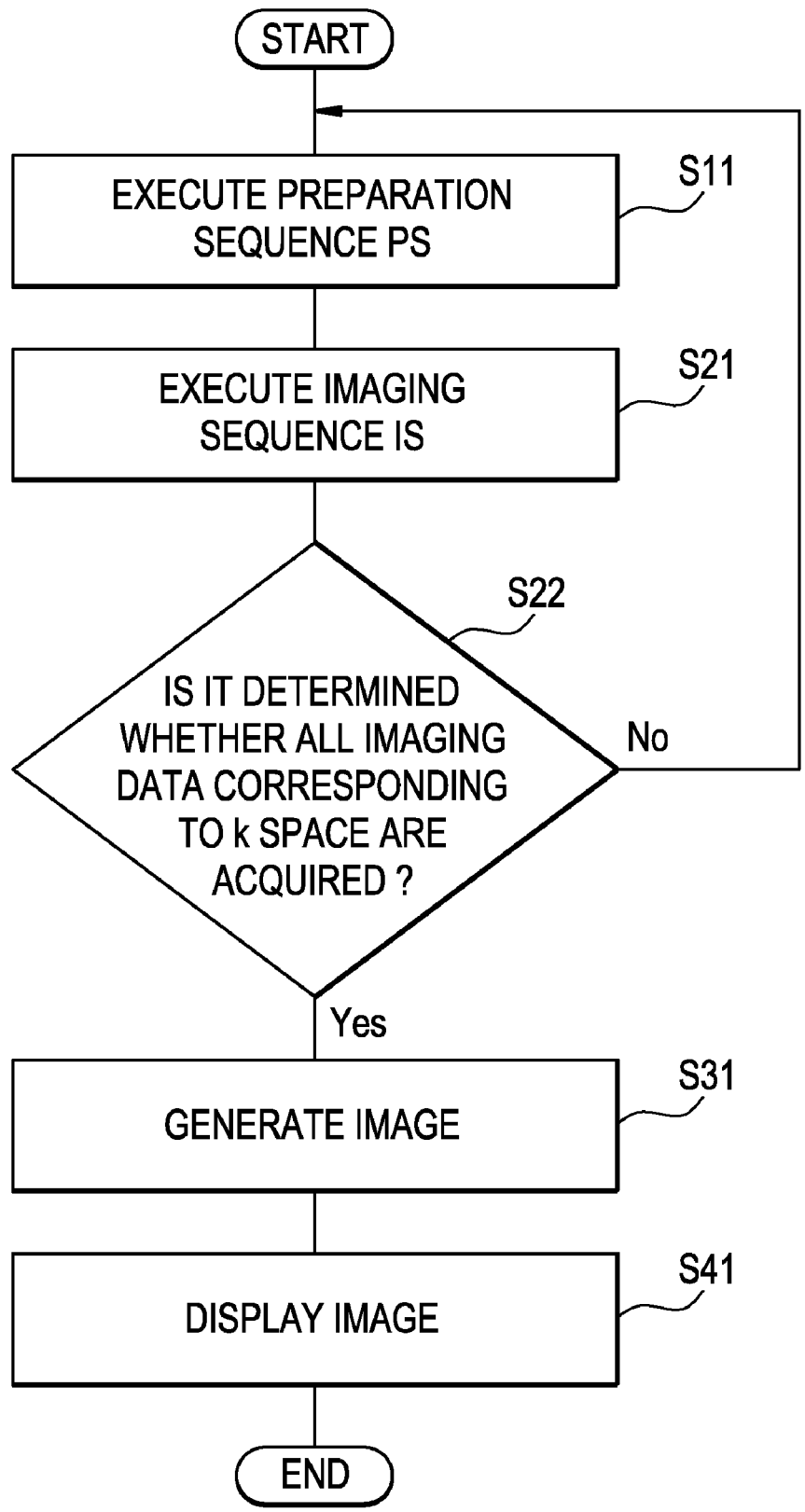
FIG. 2 is a flowchart showing operation of the first embodiment according to the invention at the time that a subject SU is photographed.

FIG. 2 is a flowchart showing operation of the first embodiment according to the invention at the time that the subject SU is photographed.

As shown in FIG. 2, a preparation sequence PS is executed (S11).

Here, the scan section 2 performs the preparation sequence PS.

Figure 3:
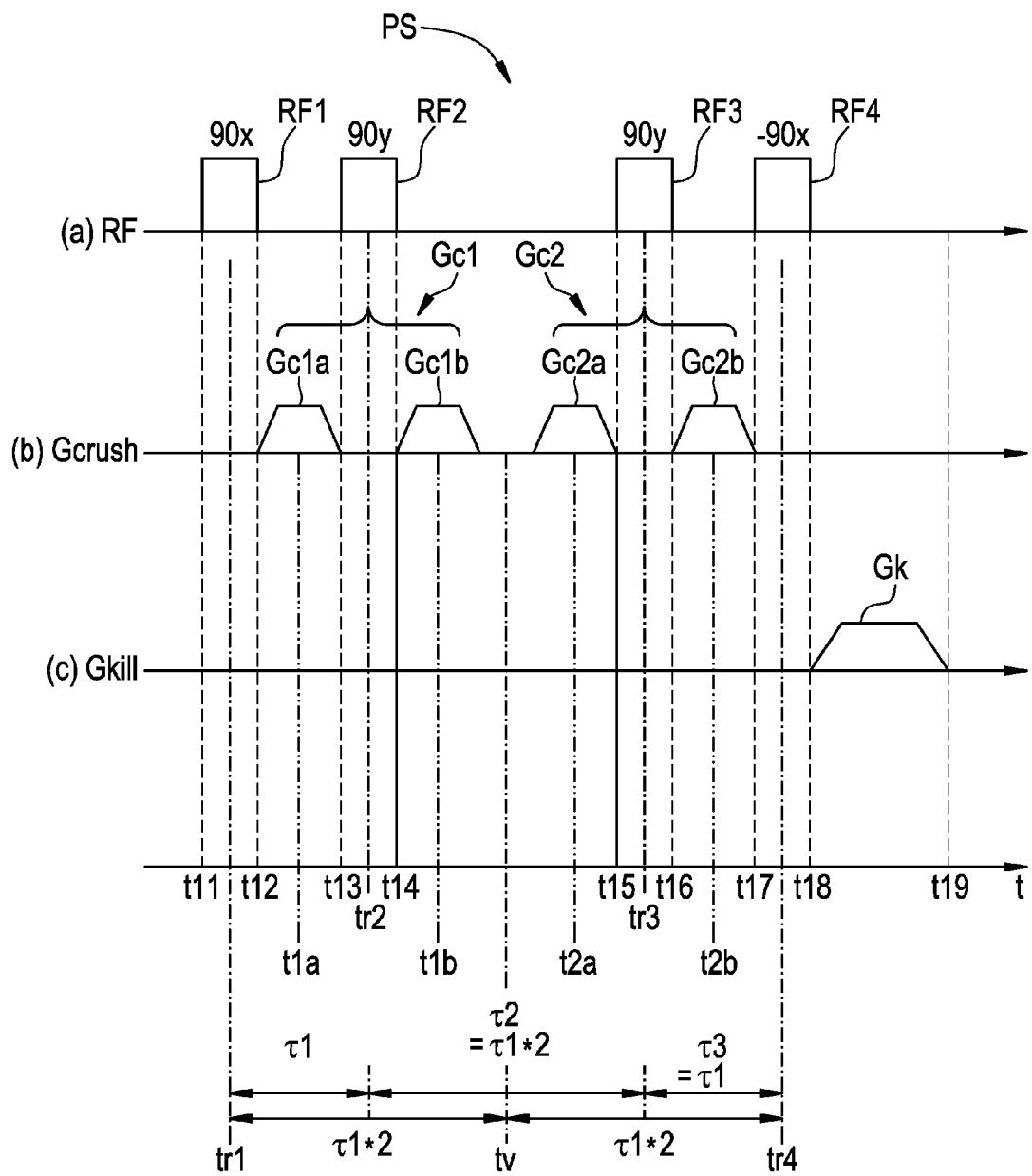
FIGS. 3(a), 3(b), and 3(c) are pulse sequence diagrams showing a preparation sequence PS in the first embodiment according to the invention.

FIG. 3 is a pulse sequence diagram showing the preparation sequence PS in the first embodiment according to the invention.

In FIG. 3, (a) indicates a time base on which RF pulses RF are transmitted, (b) indicates a time base on which crusher gradient pulses Gcrush are transmitted as gradient pulses, and (c) indicates a time base on which each of killer gradient pulses Gkill is transmitted as a gradient pulse. At the respective (a), (b) and (c), the horizontal axis indicates a time t, and the vertical axis indicates a pulse intensity, respectively. Here, Gcrush and Gkill are respectively at least one axial direction of a slice selection direction, a phase encode direction and a frequency encode direction. In the following description, a time integration value corresponds to an integration value defined by the pulse intensity and time t.

As shown in FIGS. 3(a), 3(b) and 3(c), the scan section 2 transmits a first RF pulse RF1, a second RF pulse RF2, a third RF pulse RF3, a fourth RF pulse RF4, a first crusher gradient pulse Gc1, a second crusher gradient pulse Gc2 and a killer pulse Gk to the subject SU as preparation pulses upon executing the preparation sequence PS.

As to the preparation pulses employed in the preparation sequence PS, the first RF pulse RF1, second RF pulse RF2, third RF pulse RF3 and fourth RF pulse RF4 are sequentially transmitted to the subject as rectangular pulses as shown in FIG. 3(a). That is, the four pulses corresponding to the first RF pulse RF1, the second RF pulse RF2, the third RF pulse RF3 and the fourth RF pulse RF4 are respectively sequentially transmitted to the subject at time intervals left therebetween so as to flip the spins of the subject.

Here, the scan section 2 transmits the first RF pulse RF1 and the fourth RF pulse RF4 in such a manner that as shown in FIG. 3(a), they are identical in phase to each other, the absolute values of flip angles are identical and their signs become opposite to each other. The scan section 2 transmits the first and fourth RF pulses RF1 and RF4 in such a manner that their phase are in the same x direction, the absolute values of their flip angles are 90° and identical, and their signs become opposite to each other. That is, the first RF pulse RF1 is transmitted as a 90° x pulse and the fourth RF pulse RF4 is transmitted as a −90° x pulse.

Described specifically, the first RF pulse RF1 is transmitted in such a manner that each spin of the subject is flipped at a flip angle of 90° along a yz plane including a z direction formed with a static magnetic filed and a y direction orthogonal to the z direction. That is, the spin of the subject is 90° rotated with the x direction as a central axis. The fourth RF pulse RF4 is transmitted at a flip angle of −90° in such a manner that the spin of the subject is flipped along the yz plane at 90° corresponding to the same absolute value as the first flip angle and in the direction opposite to the direction in which the spin is flipped by the transmission of the first RF pulse RF1. That is, the spin of the subject is −90° rotated with the x direction as the central axis.

The scan section 2 transmits the second RF pulse RF2 and the third RF pulse RF3 in such a manner than their phases are respectively orthogonal to the phases of the first RF pulse RF1 and the fourth RF pulse RF4 as shown in FIG. 3(a). Here, the second RF pulse RF2 and the third RF pulse RF3 are transmitted such that the absolute values of their flip angles become identical to each other. The scan section 2 transmits the second RF pulse RF2 and the third RF pulse RF3 in such a manner that the absolute values of their flip angles reach 90° corresponding to the y direction in which their phases are orthogonal to the phases of the first RF pulse RF1 and the fourth RF pulse RF4 as shown in FIG. 3(a). That is, the second RF pulse RF2 is transmitted as a 90° y pulse and the third RF pulse RF3 is transmitted as a 90° y pulse.

Described specifically, the second RF pulse RF2 is transmitted in such a manner that each spin is flipped at a flip angle of 90° along an xz plane extending along the z direction formed with the static magnetic field and the x direction orthogonal to the z and y directions. That is, the spin of the subject is 90° rotated with the y direction as a central axis. Along with it, the third RF pulse RF3 is transmitted in such a manner that the spin is flipped along the xz plane at a flip angle of 90°. That is, the spin of the subject is 90° rotated with the y direction as the central axis.

The above-described first RF pulse RF1, second RF pulse RF2, third RF pulse RF3 and fourth RF pulse RF4 are respectively sequentially transmitted to the subject in such a manner that as shown in FIG. 3(a), a second time interval τ2 between a central point of time tr2 between times t13 and t14 at which the second RF pulse RF2 is transmitted, and a central point of time tr3 between times t15 and t16 at which the third RF pulse RF3 is transmitted, is twice as much as a first time interval τ1 between a central point of time tr1 between times t11 and t12 at which the first RF pulse RF1 is transmitted, and a central point of time tr2 between times t13 and t14 at which the second RF pulse RF2 is transmitted, and a third time interval τ3 between a central point of time tr3 between times t15 and t16 at which the third RF pulse RF3 is transmitted, and a central point of time tr4 between times t17 and t18 at which the fourth RF pulse RF4 is transmitted, becomes identical to the first time interval τ1.

As to the first crusher gradient pulse Gc1 and the second crusher gradient pulse Gc2 corresponding to the preparation pulses employed in the preparation sequence PS as shown in FIG. 3(b), they are transmitted to the subject as pairs of gradient pulses Gc1a and Gc1b, and Gc2a and Gc2b in such a manner that the points of times tr2 and tr3 at which the second RF pulse RF2 and the third RF pulse RF3 are respectively transmitted are respectively interposed therebetween at the time base t.

Of the plural gradient pulses Gc1a, Gc1b, Gc2a and Gc2b transmitted as the first crusher gradient pulse Gc1 and the second crusher gradient pulse Gc2 respectively, the gradient pulse Gc1a transmitted between the first RF pulse RF1 and the second RF pulse RF2 and the gradient pulse Gc2b transmitted between the third RF pulse RF3 and the fourth RF pulse RF4 are respectively set to the same first time integration value D1 with respect to each other. Along with it, the gradient pulses Gc1b and Gc2a transmitted between the plural RF pulses transmitted as the second RF pulse RF2 and the third RF pulse RF3 respectively are respectively set to a second time integration value D2 equal to twice the first time integration value D1.

That is, when as shown in FIG. 3(b), the time integration value of the gradient pulse Gc1a is assumed to be D1a, the time integration time of the gradient pulse Gc1b is assumed to be D1b, the time integration value of the gradient pulse Gc2a is assumed to be D2a and the time integration value of the gradient pulse Gc2b is assumed to be D2b, the respective gradient pulses Gc1a, Gc1b, Gc2a and Gc2b are transmitted as the first crusher gradient pulse Gc1 and the second crusher gradient pulse Gc2 in such a manner that the following equation (1) is established.

$$2*D1a = D1b + D2a = 2*D2b \quad (1)$$

In the present embodiment, the respective gradient pulses Gc1a, Gc1b, Gc2a and Gc2b are transmitted in such a manner that their time integration values become identical to one another. That is, the pair of gradient pulses Gc1a and Gc1b that constitute the first crusher gradient pulse Gc1 and the pair of gradient pulses Gc2a and Gc2b that constitute the second crusher gradient pulse Gc2 are transmitted in such a manner that they are identical in time integration value and polarity. Namely, D1a, D1b, D2a and D2b are all set identical.

As shown in FIG. 3(b), the pair of gradient pulses Gc1a and Gc1b constituting the first crusher gradient pulse Gc1 is transmitted in such a manner that they are arranged symmetrically at the time base t with the point of time tr2 between the times t13 and t14 at which the second RF pulse RF2 is transmitted, being defined or taken as the central axis. The gradient pulse Gc1a of the pair of gradient pulses Gc1a and Gc1b constituting the first crusher gradient pulse Gc1 is transmitted in such a manner that a central point of time t1a between the times t12 and t13 at which the gradient pulse Gc1a is first transmitted, corresponds to a central point of time of the first time interval τ1 between the central point of time tr1 set between the times t11 and t12 at which the first RF pulse RF1 is transmitted, and the central point of time tr2 set between the times t13 and t14 at which the second RF pulse RF2 is transmitted.

As shown in FIG. 3(b), the pair of gradient pulses Gc2a and Gc2b constituting the second crusher gradient pulse Gc2 is transmitted in such a manner that they are arranged symmetrically about the time base t with the point of time tr3 between the times t15 and t16 at which the third RF pulse RF3 is transmitted, being defined or taken as the central axis. The gradient pulse Gc2b of the pair of gradient pulses Gc2a and Gc2b constituting the second crusher gradient pulse Gc2 is transmitted in such a manner that a central point of time t2b between the times t16 and t17 at which the gradient pulse Gc2b is transmitted subsequently, corresponds to a central point of time of the third time interval τ3 between the central point of time tr3 set between the times t15 and t16 at which the third RF pulse RF3 is transmitted, and the central point of time tr4 set between the times t17 and t18 at which the fourth RF pulse RF4 is transmitted.

In the present embodiment, the first crusher gradient pulse Gc1 constituted of the pair of gradient pulses Gc1a and Gc1b is transmitted to the subject with the central point of time tr2 at which the second RF pulse RF2 is transmitted, being interposed therebetween at the time base t and the second crusher gradient pulse Gc2 constituted of the pair of gradient pulses Gc2a and Gc2b is transmitted to the subject with the central point of time tr3 at which the third RF pulse RF3 is transmitted, being interposed therebetween at the time base t, in such a manner that the phase of a second spin echo signal SE22 generated from a second spin held in a moving state is shifted with respect to the phase of a first spin echo SE21 generated from a first spin held in a stationary state by the transmission of the first RF pulse RF1, the second RF pulse RF2 and the third RF pulse RF3, and the phase of a second stimulated echo signal STE2 generated from the second spin held in the moving state is shifted with respect to the phase of a first stimulated echo signal STE1 generated from the first spin held in the stationary state.

Here, a spin echo signal SE1 is generated by the transmission of the first RF pulse RF1 and the second RF pulse RF2 at a point of time tv when the time interval (τ1*2) equal to twice the first time interval τ1 between the central point of time tr1 set between the times t11 and t12 at which the first RF pulse RF1 is transmitted, and the central point of time tr2 set between the times t13 and t14 at which the second RF pulse RF2 is transmitted, has elapsed from the central point of time tr1 between the times t11 and t12 at which the first RF pulse RF1 is transmitted.

Thereafter, since the spin echo signal SE1 is refocused by the third RF pulse RF3, another spin echo signal SE2 is generated at a point of time tr4 when a time interval (τ1*4) equal to four times the first time interval τ1 between the central point of time tr1 set between the times t11 and t12 at which the first RF pulse RF1 is transmitted, and the central point of time tr2 set between the times t13 and t14 at which the second RF pulse RF2 is transmitted, has elapsed from the central point of time tr1 between the times t11 and t12 at which the first RF pulse RF1 is transmitted. That is, a spin echo signal SE2 is generated at the central point of time tr4 between the times t17 and t18 at which the fourth RF pulse RF4 is transmitted.

At this time, the spin echo signal SE22 generated from the second spin held in the moving state is shifted in phase by the pair of gradient pulses Gc1a and Gc1b constituting the first crusher gradient pulse Gc1 and the pair of gradient pulses Gc2a and Gc2b constituting the second crusher gradient pulse Gc2, whereas the spin echo signal SE21 generated from the first spin held in the stationary state is not shifted in phase. Therefore, the spin echo signal SE22 results in a state in which the phase of the spin echo signal SE22 generated from the second spin held in the moving state is shifted with respect to the phase of the spin echo signal SE21 generated from the first spin held in the stationary state. Thus, since the spin echo signal SE2 is shifted in phase according to the velocity at which the second spin held in the moving state moves, it has a phase.

On the other hand, a stimulated echo signal STE is generated by the transmission of the first RF pulse RF1, the second RF pulse RF2 and the third RF pulse RF3 at the point of time tr4 at which the spin echo signal SE2 is generated.

At this time, a stimulated echo signal STE2 generated from the second spin held in the moving state is shifted in phase by the previously-transmitted gradient pulse Gc1a of the pair of gradient pulses Gc1a and Gc1b constituting the first crusher gradient pulse Gc1 and the subsequently-transmitted gradient pulse Gc2b of the pair of gradient pulses Gc2a and Gc2b constituting the second crusher gradient pulse Gc2, whereas a stimulated echo signal STE1 generated from the first spin held in the stationary state is not shifted in phase. Therefore, the stimulated echo signal STE2 is brought to a state in which the phase of the stimulated echo signal STE2 generated from the second spin held in the moving state is shifted with respect to the phase of the stimulated echo signal STE1 generated from the first spin held in the stationary state. Thus, since the stimulated echo signal STE is shifted in phase according to the velocity at which the second spin held in the moving state moves, it assumes a phase.

After the fourth RF pulse RF4 has been transmitted as shown in FIG. 3(c) and the crusher gradient pulses Gc1 and Gc2 respectively constituted of the pairs of gradient pulses Gc1a and Gc1b and Gc2a and Gc2b have been transmitted as described above, the killer gradient pulse Gk is transmitted to the subject. That is, the killer gradient pulse Gk is transmitted to the subject in such a manner that a gradient magnetic field for causing transverse magnetization of each spin to disappear is generated, from the point of time t18 subsequent to the transmission of the second crusher gradient pulse Gc2 and the transmission of the fourth RF pulse RF4 to a point of time t19 at which a predetermined time interval has elapsed from the point of time t18.

Figure 4:
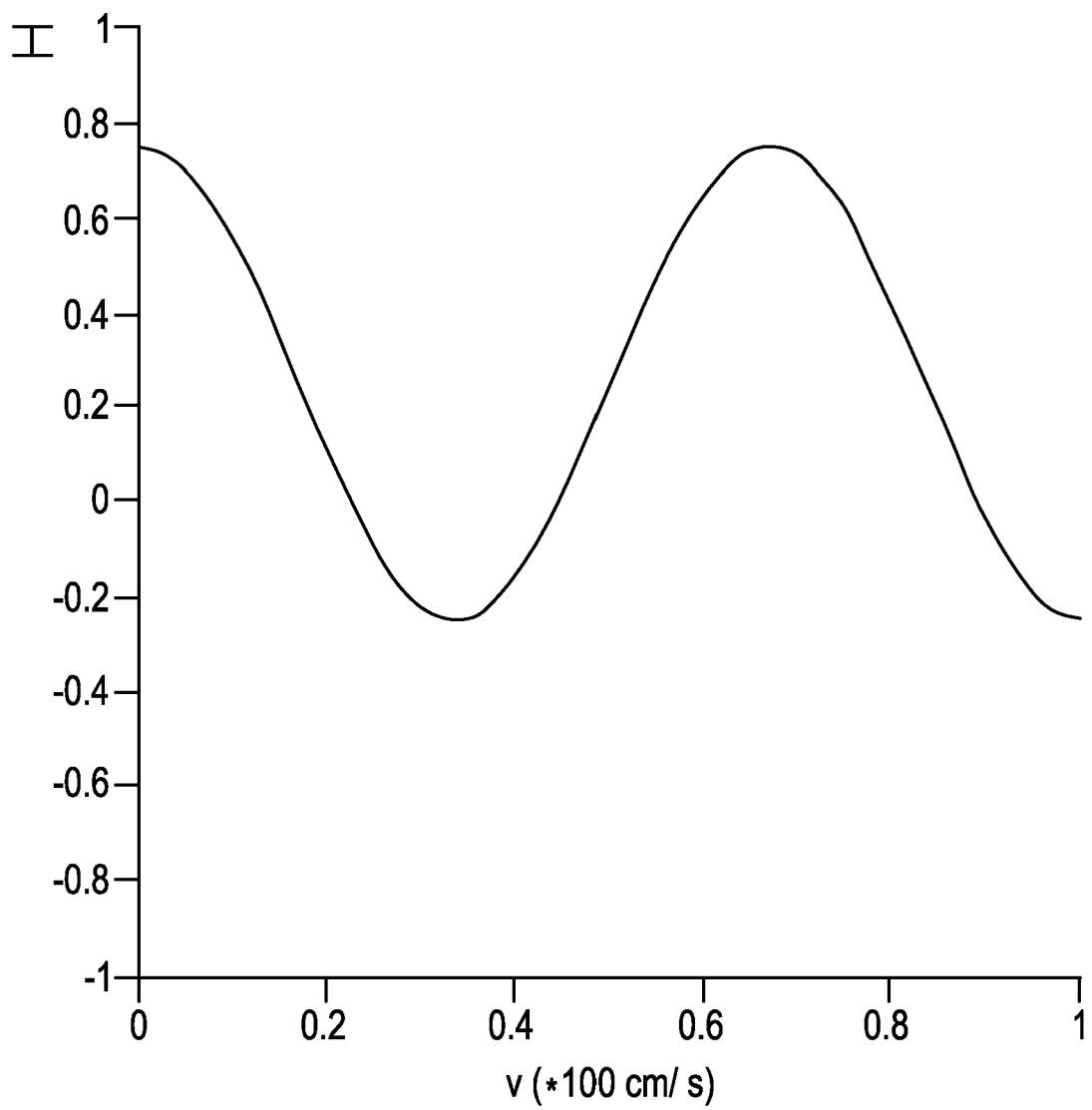
FIG. 4 is a diagram illustrating, in graph form, a result of simulation of the relationship between a signal intensity obtained at a time t19 subsequent to execution of the preparation sequence PS and the velocity of each spin moved within the subject in the first embodiment according to the invention.

FIG. 4 is a diagram showing, in graph form, a result of simulation of the relationship between a signal intensity obtained at the point of time t19 subsequent to execution of the preparation sequence PS and the velocity of each spin moved within the subject in the first embodiment according to the invention.

In FIG. 4, the horizontal axis indicates a velocity v (*100 cm/s) at which the spin moves, and the vertical axis indicates a signal intensity I, respectively. Incidentally, magnetization of the spin that passes through the origin of the Gcrush axis at the central point of time t1a at which the gradient pulse Gc1a is transmitted, is moved on the Gcrush axis by constant-velocity linear motion in the preparation sequence PS shown in FIG. 3 here. Assuming that the phase incurred by the gradient pulse Gc1b is π at the central point of time t1b at which the gradient pulse Gc1b is transmitted, when the magnetization of the spin is moved at the velocity of 100 cm/s, simulation is done. Here, it means that when the signal intensity is 1, the magnetization is perfectly brought to a thermal equilibrium state, and T2 attenuation is not taken into consideration.

In the present embodiment as shown in FIG. 4, each obtained signal intensity varies according to the velocity of each spin moved within the subject. Described specifically, the first spin which is zero in velocity and held in the stationary state, is brought to a signal intensity of about 0.8 as shown in FIG. 4. The second spin whose velocity is 100 cm/s, for example, is brought to a signal intensity of about −0.2.

This phenomenon will be explained. As mentioned above, the phases of the second spins each held in the moving state, corresponding to the spin echo signal SE2 and stimulated echo signal STE generated at the central point of time tr4 (see FIG. 3) between the times t17 and t18 at which the fourth RF pulse RF4 is transmitted, are shifted according to their moving velocities. Therefore, since the phase $\theta_{SE2}$ of the spin echo signal SE2 and the phase $\theta_{STE}$ of the stimulated echo signal STE are canceled each other where they are different in moving velocity, its influence is exerted upon each signal intensity. Therefore, the obtained signal intensity differs according to the velocity of each spin moved within the subject as shown in FIG. 4.

Next, an imaging sequence IS is executed as shown in FIG. 2 (S21).

Here, the scan section 2 executes the imaging sequence IS by the SSFP type imaging method.

Figure 5:
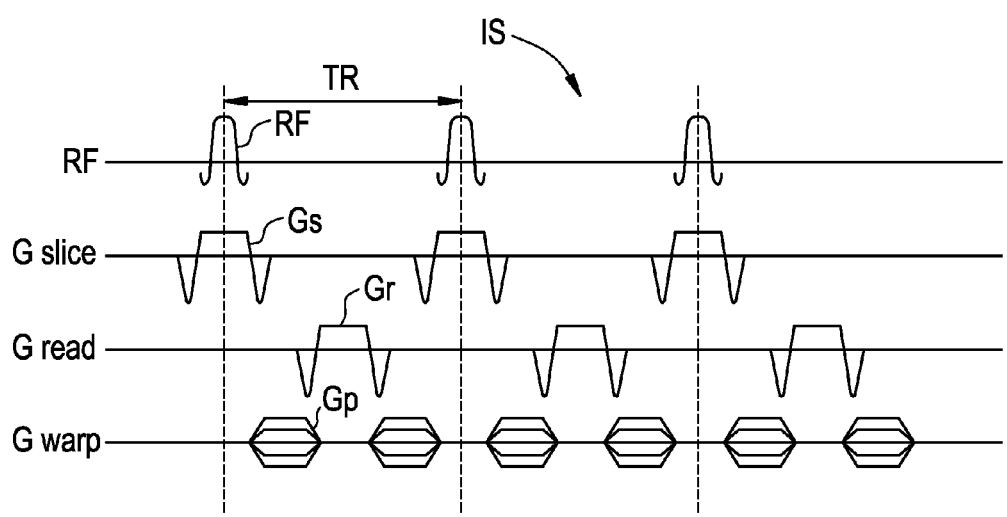
FIG. 5 is a pulse sequence diagram showing an imaging sequence IS executed in the first embodiment according to the invention.

FIG. 5 is a pulse sequence diagram showing the imaging sequence IS executed in the first embodiment according to the invention.

In FIG. 5, RF indicates a time base on which RF pulses are transmitted, Gslice indicates a time base on which gradient pulses are transmitted in a slice selection encode direction, Gread indicates a time base on which gradient pulses are transmitted in a readout direction, and Gwarp indicates a time base on which gradient pulses are transmitted in a phase encode direction. In the respective RF, Gslice, Gread and Gwarp, the horizontal axis indicates a time t, and the vertical axis indicates a pulse intensity.

Upon execution of the imaging sequence IS as shown in FIG. 5, the RF pulses are repeatedly transmitted to the subject SU. Here, the scan section 2 transmits the respective RF pulses RF to the subject SU at such time of repetition TR that longitudinal magnetization of each spin in the subject SU and transverse magnetization thereof are respectively brought to a steady state.

Along with it, a slice selection gradient pulse Gs for selecting a slice of the subject SU, which is excited by the corresponding RF pulse RF, as an imaging area, a phase encode gradient pulse Gr for phase-encoding a magnetic resonance signal generated at the slice excited by the RF pulse, and a frequency encode gradient pulse for frequency-encoding the magnetic resonance signal generated at the slice excited by the RF pulse are transmitted to the subject SU as gradient pulses within the time of repetition TR. Here, the slice selection gradient pulse, the phase encode gradient pulse and the frequency encode gradient pulse are transmitted to the subject SU such that a time integration value becomes zero within the time of repetition TR. That is, as shown in FIG. 5, the transverse magnetization is rewound within the time of repetition TR after acquisition of each magnetic resonance signal as imaging data, and the phase encoded by its corresponding gradient field is reset.

Next, it is determined whether all imaging data corresponding to k space are acquired as shown in FIG. 2 (S22).

Here, the controller 30 determines whether all imaging data corresponding to the k space are acquired.

When all the imaging data corresponding to the k space are not acquired (No), the execution (S11) of the preparation sequence PS and the execution (S21) of the imaging sequence IS are sequentially made again as shown in FIG. 2. That is, the execution (S11) of the preparation sequence PS and the execution (S21) of the imaging sequence IS are repeatedly made, thereby acquiring imaging data until the k space is all filled up.

On the other hand, when all the imaging data are acquired so as to correspond to the k space (Yes), the generation of each image is done as shown in FIG. 2 (S31).

Here, the scan section 2 sets the imaging data obtained by executing the imaging sequence IS as raw data, and the image generator 31 reconstructs each image about the subject SU.

In the present embodiment, the signal intensities each obtained according to the velocity of each spin moved within the subject differ after the preparation sequence PS has been executed as mentioned above (see FIG. 4). Therefore, each spin held in the stationary state has large longitudinal magnetization. For example, the longitudinal magnetization of each spin held in a moving state, which moves at a velocity of 100 cm/s, becomes smaller. Hence, there is a large difference therebetween. Therefore, an image set high in contrast between a portion held in a stationary state and a portion held in a moving state is generated at images image-reconstructed based on the imaging data obtained by executing the imaging sequence IS after execution of the preparation sequence PS. Described specifically, an MRA image is generated in which an organ portion at which the spin is in the stationary state and a blood portion at which the spin is in the moving state, are high in contrast.

Next, the image is displayed as shown in FIG. 2 (S41).

Here, the display unit 33 receives data about each image of the subject SU from the image generator 31 and displays the image on its display screen.

In the present embodiment as described above, the preparation sequence PS for transmitting the preparation pulses to the subject in such a manner that the signal intensity of each magnetic resonance signal obtained according to the velocity of each spin moved in the subject differs, is executed prior to the execution of the imaging sequence IS. Here, the first RF pulse RF1, the second RF pulse RF2, the third RF pulse RF3 and the fourth RF pulse RF4 are respectively sequentially transmitted to the subject as the preparation pulses. Along with it, the crusher gradient pulses Gc1 and Gc2 are respectively transmitted to the subject in such a manner that the points of times tr2 and tr3 at which the second RF pulse RF2 and the third RF pulse RF3 are respectively transmitted, are interposed at the time base t. After the crusher gradient pulses Gc1 and Gc2 have been transmitted after the transmission of the fourth RF pulse RF4, the killer gradient pulse Gk is transmitted to the subject. Therefore, the signal intensity obtained depending on the velocity of each spin moved within the subject differs after execution of the preparation sequence PS as described above. Thus, images different in luminance depending on the moving velocity of each spin are generated at the images image-reconstructed based on the imaging data obtained by executing the imaging sequence IS after the execution of the preparation sequence PS.

Therefore, the present embodiment is capable of obtaining the images in which portions each moved at a predetermined moving velocity are emphasized at the subject SU. For instance, the MRA image high in contrast between the organ portion in which the spin is in the stationary state and the blood portion in which the spin is in the moving state can be generated. This is because the amount of dephase between the stimulated echo signal and the spin echo signal based on the magnetization of each spin being moved in the Gcrush direction changes by the crusher gradient pulses Gc1 and Gc2, and the signal intensity is lowered so that flow voids are generated.

Further, since the time provided to apply each of the preparation pulses is short, the present embodiment can be made available for various uses.

In the present embodiment, the first RF pulse RF1 and the fourth RF pulse RF4 are transmitted as the 90° x pulse and the −90° x pulse. Therefore, the magnetization of each spin held in the stationary state can be held, and the magnetization of each spin held in the moving state can be distributed to an intensity ranging from 0 or less to 1. It is therefore possible to generate a high-contrast image depending on the moving speed of the spin.

Thus, the present embodiment is capable of enhancing general versatility without using a contrast agent and improving image quality.

Second embodiment. A second embodiment according to the invention will be explained below.

Figure 6:
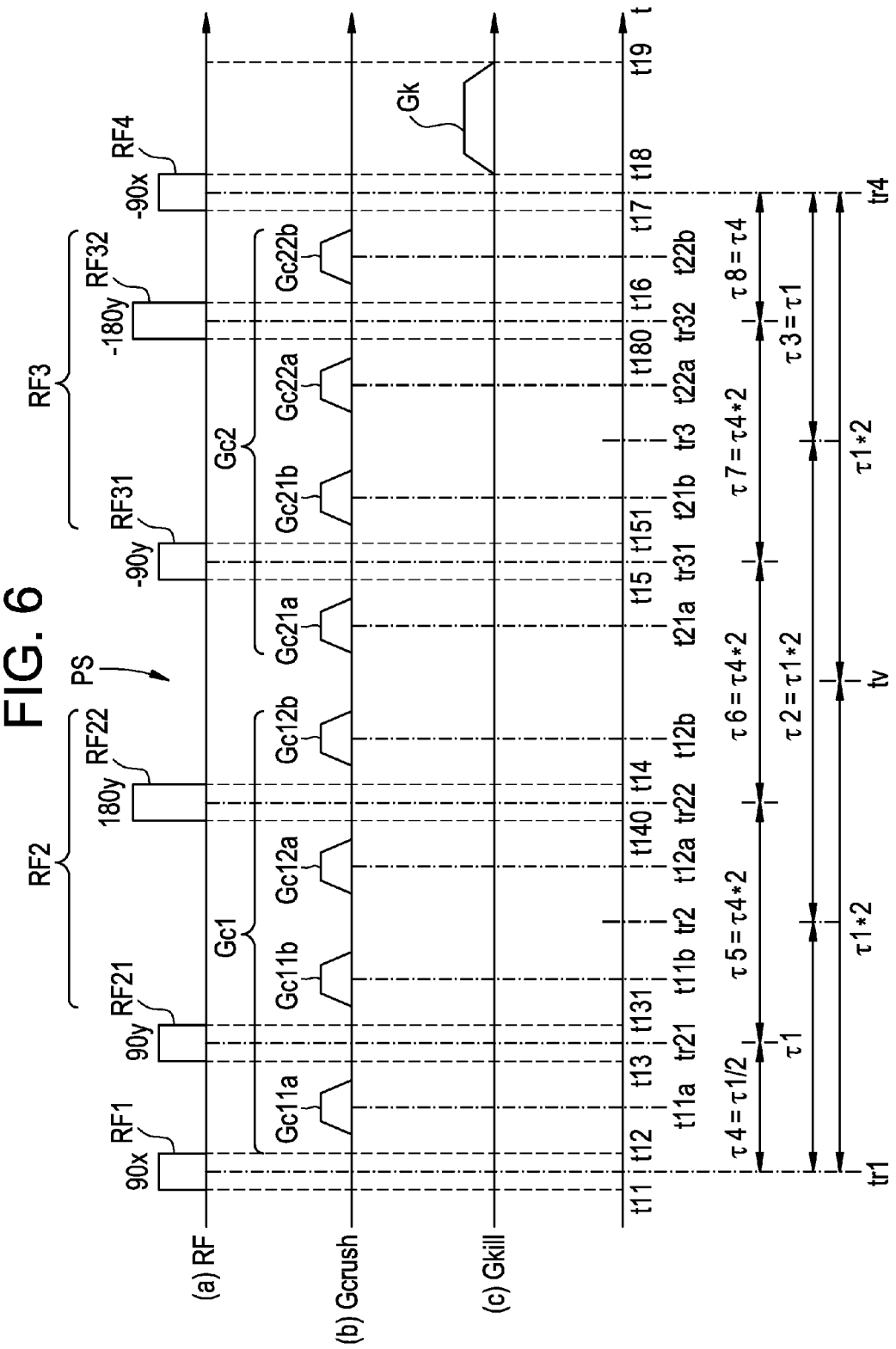
FIGS. 6(a), 6(b), and 6(c) are pulse sequence diagrams illustrating a preparation sequence PS in a second embodiment according to the invention.

FIG. 6 is a pulse sequence diagram showing a preparation sequence PS executed in the second embodiment according to the invention.

In FIG. 6, (a) indicates a time base on which RF pulses RF are transmitted, (b) indicates a time base on which crusher gradient pulses Gcrush are transmitted as gradient pulses, and (c) indicates a time base on which each of killer gradient pulses Gkill is transmitted as a gradient pulse. At the respective (a), (b) and (c), the horizontal axis indicates a time t, and the vertical axis indicates a pulse intensity, respectively. Here, Gcrush and Gkill are respectively at least one axial direction of a slice selection direction, a phase encode direction and a frequency encode direction.

As shown in FIG. 6, the present embodiment is different from the first embodiment in terms of the preparation sequence PS executed upon photographing a subject SU. The present embodiment is similar to the first embodiment except for this point. Therefore, explanation of dual portions or points will be omitted.

As shown in FIGS. 6(a), 6(b) and 6(c), the scan section 2 transmits a first RF pulse RF1, a second RF pulse RF2, a third RF pulse RF3, a fourth RF pulse RF4, a first crusher gradient pulse Gc1, a second crusher gradient pulse Gc2 and a killer pulse Gk to the subject SU as preparation pulses upon executing the preparation sequence PS in a manner similar to the first embodiment.

However, in the present embodiment unlike the first embodiment, as shown in FIG. 6(a), a plurality of RF pulses RF21 and RF22 including a 180° pulse are transmitted as a second RF pulse RF2, and a plurality of RF pulses RF31 and RF32 including a 180° pulse are transmitted as a third RF pulse RF3.

Here, the plurality of RF pulses RF21, RF22, RF31 and RF33 respectively transmitted as the second RF pulse RF2 and third RF pulse RF3 are transmitted in such a manner that their phases are identical to one another, the absolute values of their flip angles are the same, and their signs are reversed.

In the present embodiment, α° pulses RF21 and RF31 and 180° pulses RF22 and RF32 excluding the 180° pulses are sequentially transmitted as the plurality of RF pulses RF21, RF22, RF31 and RF32 respectively transmitted for the second RF pulse RF2 and the third RF pulse RF3.

Described specifically, as the plurality of RF pulses RF21 and RF22 transmitted as the second RF pulse RF2, as shown in FIG. 6(a), a 90° y pulse in which the absolute value of its flip angle is 90°, its sign is plus and its phase is in a y direction, is transmitted as a first α° pulse RF21, and a 180° y pulse in which the absolute value of its flip angle is 180°, its sign is plus and its phase is in the y direction, is transmitted as a first 180° pulse RF22. That is, as the plurality of RF pulses RF21 and RF22 transmitted as the second RF pulse RF2, the first α° pulse RF21 and the first 180° pulse RF22 other than the 180° pulse are transmitted along an xz plane such that each spin is flipped.

As the plurality of RF pulses RF31 and RF32 transmitted as the third RF pulse RF3, as shown in FIG. 6(a), a −90° y pulse in which the absolute value of its flip angle is 90°, its sign is minus and its phase is in the y direction, is transmitted as a second α° pulse RF31, and a −180° y pulse in which the absolute value of its flip angle is 180°, its sign is minus and its phase is in the y direction, is transmitted as a second 180° pulse RF32. That is, as the plurality of RF pulses RF31 and RF32 transmitted as the third RF pulse RF3, both the second α° pulse RF31 identical in flip angle to the first α° pulse RF21, and the second 180° pulse RF32 other than the 180° pulse are transmitted along the xz plane in the direction opposite to the direction in which each spin is flipped by transmission of the second RF pulse RF2, such that each spin is flipped.

Here, as shown in FIG. 6(a), the first RF pulse RF1 and the first α° pulse RF21 and first 180° pulse RF22 used as the second RF pulse RF2 are respectively sequentially transmitted to the subject in such a manner that a fifth time interval τ5 between a central point of time tr21 between times t13 and t131 at which the first α° pulse RF21 is transmitted, and a central point of time tr22 between times t140 and t14 at which the first 180° pulse RF22 is transmitted, becomes twice as much as a fourth time interval τ4 between a central point of time tr1 between times t11 and t12 at which the first RF pulse RF1 is transmitted, and a central point of time tr21 between times t13 and t131 at which the first α° pulse RF21 is transmitted. The second α° pulse RF31 and second 180° pulse RF32 used as the third RF pulse RF3, and the fourth RF pulse RF4 are respectively sequentially transmitted to the subject in such a manner that a sixth time interval τ6 between a central point of time tr22 between times t140 and t14 at which the first 180° pulse RF22 is transmitted, and a central point of time tr31 between times t15 and t151 at which the second α° pulse RF31 is transmitted, is equal to twice the fourth time interval τ4, a seventh time interval τ7 between the central point of time tr31 set between the times t15 and t151 at which the second α° pulse RF31 is transmitted, and a central point of time tr32 set between times t160 and t16 at which the second 180° pulse RF32 is transmitted, is equal to twice the fourth time interval τ4, and an eighth time interval τ8 between the central point of time tr32 set between the times t160 and t16 at which the second 180° pulse RF32 is transmitted and a central point of time tr4 set between times t17 an t18 at which the fourth RF pulse RF4 is transmitted, becomes identical to the fourth time interval τ4.

In the present embodiment as shown in FIG. 6(b), the first crusher gradient pulse Gc1 and the second crusher gradient pulse Gc2 used as the preparation pulses employed in the preparation sequence PS are transmitted to the subject as pairs of gradient pulses Gc11a, Gc11b, Gc12a and Gc12b, and Gc21a, Gc21b, Gc22a and Gc22b in such a manner that the points of times tr2 and tr3 at which the second RF pulse RF2 and the third RF pulse RF3 are respectively transmitted, are interposed at the time base t, in a manner similar to the first embodiment.

Described specifically, when the time integration value of the gradient pulse Gcd1a, the time integration value of the gradient pulse Gcd1b, the time integration value of the gradient pulse Gc12a, the time integration value of the gradient pulse Gc12b, the time integration value of the gradient pulse Gc21a, the time integration value of the gradient pulse Gc21b, the time integration value of the gradient pulse Gc22a, and the time integration value of the gradient pulse Gc22b are respectively assumed to be D11a, D11b, D12a, D12b, D21a, D21b, D22a and D22b, the respective gradient pulses Gc11a, Gc11b, Gc12a, Gc12b, Gc21a, Gc21b, Gc22a and Gc22b are transmitted as the first crusher gradient pulse Gc1 and the second crusher gradient pulse Gc2 in such a manner that the following equation (2) is established.

$$2*D11a = D11b + D12a = D12b + D21a = D21b + D22a = 2*D22b \quad (2)$$

In the present embodiment, as shown in FIG. 6(b), the respective pairs of gradient pulses Gc11a, Gc11b, Gc12a and Gc12b that constitute the first crusher gradient pulse Gc1, and the respective pairs of gradient pulses Gc21a, Gc21b, Gc22a and Gc22b that constitute the second crusher gradient pulse Gc2 are transmitted in such a manner that they are identical in time integration value and in polarity respectively. That is, D11a, D11b, D12a, D12b, D21a, D21b, D22a and D22b are all set identical to one another.

Here, as shown in FIG. 6(b), the pairs of gradient pulses Gcd11a, Gcd11b, Gc12a and Gc12b constituting the first crusher gradient pulse Gc1 are respectively transmitted in such a manner that they are arranged symmetrically at the time base t with the point of time tr2 between the times t13 and t14 at which the second RF pulse RF2 is transmitted, being defined as the central axis. That is, the pair of gradient pulses Gcd11a and Gc11b is sequentially transmitted in such a manner that they are arranged symmetrically with the central point of time tr21 set between the times t13 and t131 at which the first $\alpha°$ pulse RF21 for the second RF pulse RF2 is transmitted, being interposed therebetween at the time base. The pair of gradient pulses Gc12a and Gc12b is sequentially transmitted in such a manner that they are arranged symmetrically with the central point of time tr22 set between the times t140 and t14 at which the first 180° pulse RF22 is transmitted, being interposed therebetween at the time base.

As shown in FIG. 6(b), the pairs of gradient pulses Gc21a, Gc21b, Gc22a and Gc22b constituting the second crusher gradient pulse Gc2 are respectively transmitted in such a manner that they are arranged symmetrically at the time base t with the point of time tr3 between the times t15 and t16 at which the third RF pulse RF3 is transmitted, being defined as the central axis. That is, the pair of gradient pulses Gc21a and Gc21b is sequentially transmitted in such a manner that they are arranged symmetrically with the central point of time tr31 set between the times t15 and t151 at which the second $\alpha°$ pulse RF31 for the third RF pulse RF3 is transmitted, being interposed therebetween at the time base. The pair of gradient pulses Gc22a and Gc22b is sequentially transmitted in such a manner that they are arranged symmetrically with the central point of time tr32 set between the times t160 and t16 at which the second 180° pulse RF32 is transmitted, being interposed therebetween at the time base.

Figure 7:
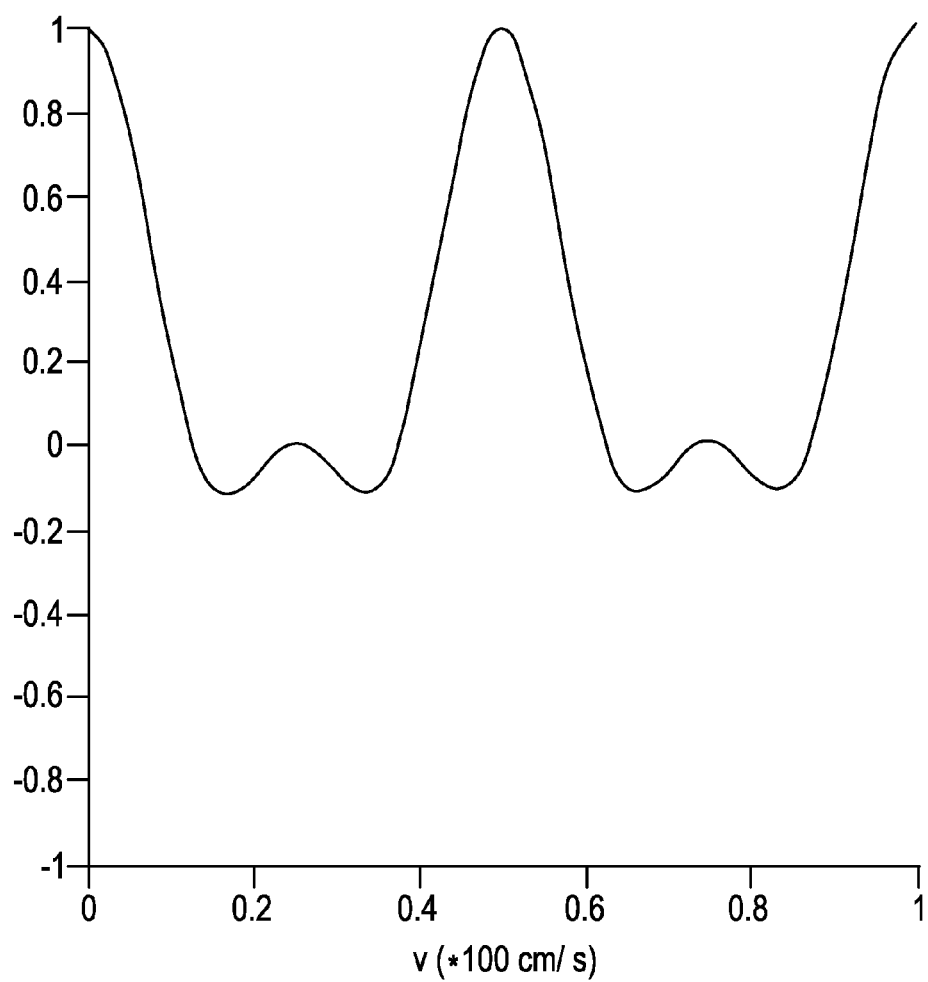
FIG. 7 is a diagram illustrating, in graph form, a result of simulation of the relationship between a signal intensity obtained at a time t19 subsequent to execution of the preparation sequence PS and the velocity of each spin moved within a subject in the second embodiment according to the invention.

FIG. 7 is a diagram illustrating, in graph form, a result of simulation of the relationship between a signal intensity obtained at a time t19 subsequent to execution of the preparation sequence PS and the velocity of each spin moved within a subject in the second embodiment according to the invention.

In FIG. 7, the horizontal axis indicates a velocity v (*100 cm/s) at which each spin moves, and the vertical axis indicates a signal intensity I. Simulation is carried out in a manner similar to the first embodiment.

In the present embodiment as shown in FIG. 7, each obtained signal intensity differs according to the velocity of each spin moved within the subject in a manner similar to the first embodiment. Described specifically, as shown in FIG. 7, a first spin held in a stationary state, which is zero in velocity, is brought to a signal intensity of about 1.0. A second spin whose velocity is 85 cm/s, for example, is brought to a signal intensity of about −0.1.

In the present embodiment as described above, the plurality of RF pulses RF1 and RF22 including the 180° pulses are transmitted as the second RF pulse RF2. The plurality of RF pulses RF31 and RF32 including the 180° pulses are transmitted as the third RF pulse RF3. Therefore, the present embodiment is capable of obtaining images in which portions each moved at a predetermined moving velocity are emphasized at the subject SU, in a manner similar to the first embodiment. For instance, an MRA image high in contrast between an organ portion in which the spin is in a stationary state and a blood portion in which the spin is in a moving state can be generated.

In the present embodiment in particular, as to magnetization of each spin held in the stationary state, which is zero in velocity, a spin echo signal and a stimulated echo signal are perfectly refocused by a 180° y pulse. Thus, since their signal intensities are obtained as about 1.0, the present embodiment is easy to generate an image at a high luminance as compared with the first embodiment.

Thus, the present embodiment is capable of enhancing general versatility without using a contrast agent and improving image quality in a manner similar to the first embodiment.

Third embodiment. A third embodiment according to the invention will be explained below.

Figure 8:
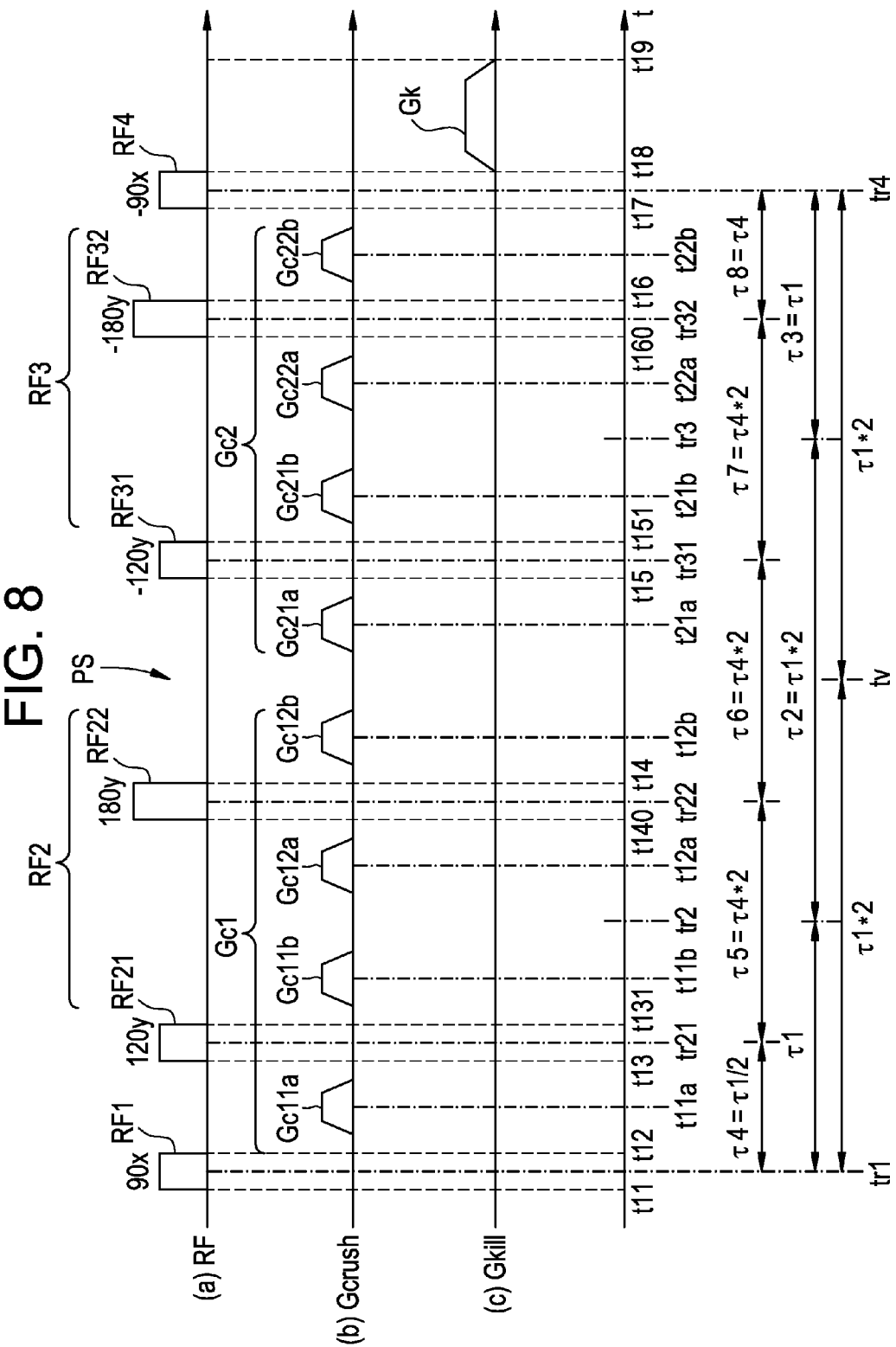
FIGS. 8(a), 8(b), and 8(c) are pulse sequence diagrams showing a preparation sequence PS in a third embodiment according to the invention.

FIG. 8 is a pulse sequence diagram showing a preparation sequence PS in the third embodiment according to the invention.

In FIG. 8, (a) indicates a time base on which RF pulses RF are transmitted, (b) indicates a time base on which crusher gradient pulses Gcrush are transmitted as gradient pulses, and (c) indicates a time base on which each of killer gradient pulses Gkill is transmitted as a gradient pulse. At the respective (a), (b) and (c), the horizontal axis indicates a time t, and the vertical axis indicates a pulse intensity, respectively. Here, Gcrush and Gkill are respectively at least one axial direction of a slice selection direction, a phase encode direction and a frequency encode direction.

As shown in FIG. 8, the present embodiment is different from the second embodiment in terms of the absolute values of flip angles of a first $\alpha°$ pulse RF21 and a second $\alpha°$ pulse RF31 in the preparation sequence PS executed upon photographing a subject SU. The present embodiment is similar to the second embodiment except for this point. Therefore, explanation of dual portions or points will be omitted.

In the present embodiment, the absolute values of the flip angles of the first $\alpha°$ pulse RF21 and the second $\alpha°$ pulse RF31 are set as 120° as shown in FIG. 8(a) unlike the second embodiment. That is, the first $\alpha°$ pulse RF21 is transmitted as a 120° y pulse, and the second $\alpha°$ pulse RF31 is transmitted as a −120° y pulse.

Figure 9:
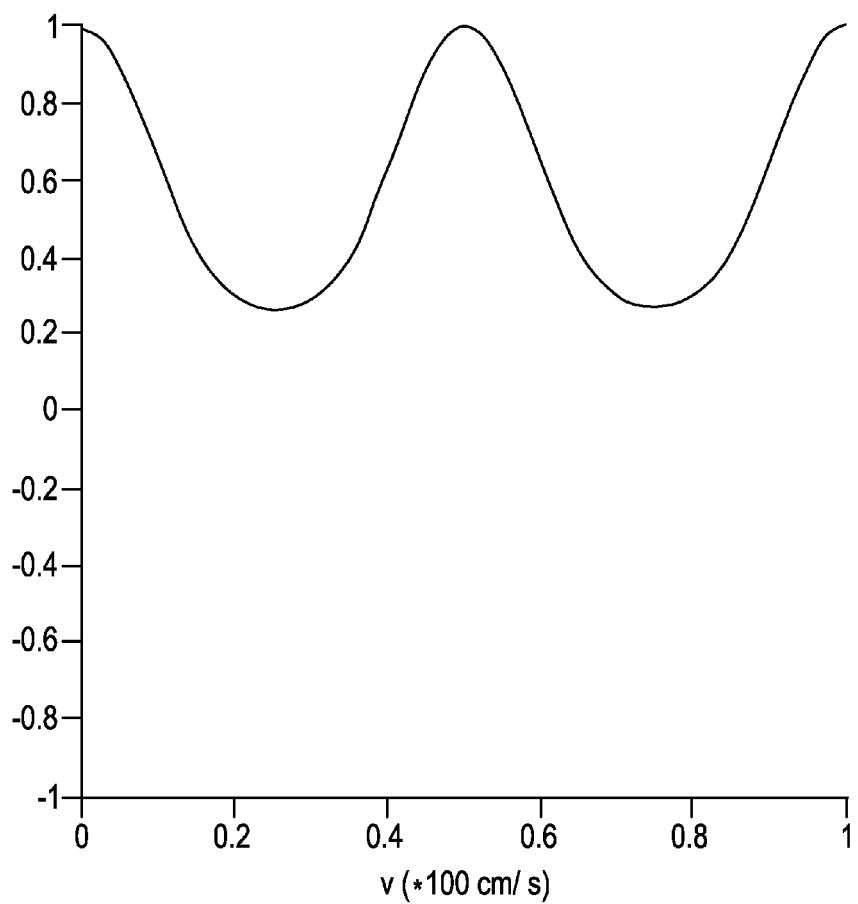
FIG. 9 is a diagram illustrating, in graph form, a result of simulation of the relationship between a signal intensity obtained at a time t19 subsequent to execution of the preparation sequence PS and the velocity of each spin moved within a subject in the third embodiment according to the invention.

FIG. 9 is a diagram illustrating, in graph form, a result of simulation of the relationship between a signal intensity obtained at a point of time t19 subsequent to execution of the preparation sequence PS and the velocity of each spin moved within a subject in the third embodiment according to the invention.

In FIG. 9, the horizontal axis indicates a velocity v (*100 cm/s) at which each spin moves, and the vertical axis indicates a signal intensity I. Simulation is carried out in a manner similar to the first embodiment.

In the present embodiment as shown in FIG. 9, each obtained signal intensity differs according to the velocity of each spin moved within the subject in a manner similar to the second embodiment. Described specifically, as shown in FIG. 9, a first spin held in a stationary state, which is zero in velocity, is brought to a signal intensity of about 1.0. A second spin whose velocity is 75 cm/s, for example, is brought to a signal intensity of about 0.3.

In the present embodiment as described above, the plurality of RF pulses RF1 and RF22 including the 180° pulses are transmitted as the second RF pulse RF2. The plurality of RF pulses RF31 and RF32 including the 180° pulses are transmitted as the third RF pulse RF3. Since the absolute values of the flip angles of the first $\alpha°$ pulse RF21 and the second $\alpha°$ pulse RF31 are respectively set as 120° in particular, the amount of generation of a stimulated echo signal can be increased, thus making it possible to enhance the effects of the crusher gradient pulses Gc1 and Gc2.

Thus, the present embodiment is capable of enhancing general versatility without using a contrast agent and improving image quality in a manner similar to the second embodiment.

Fourth embodiment. A fourth embodiment according to the invention will be explained below.

Figure 10:
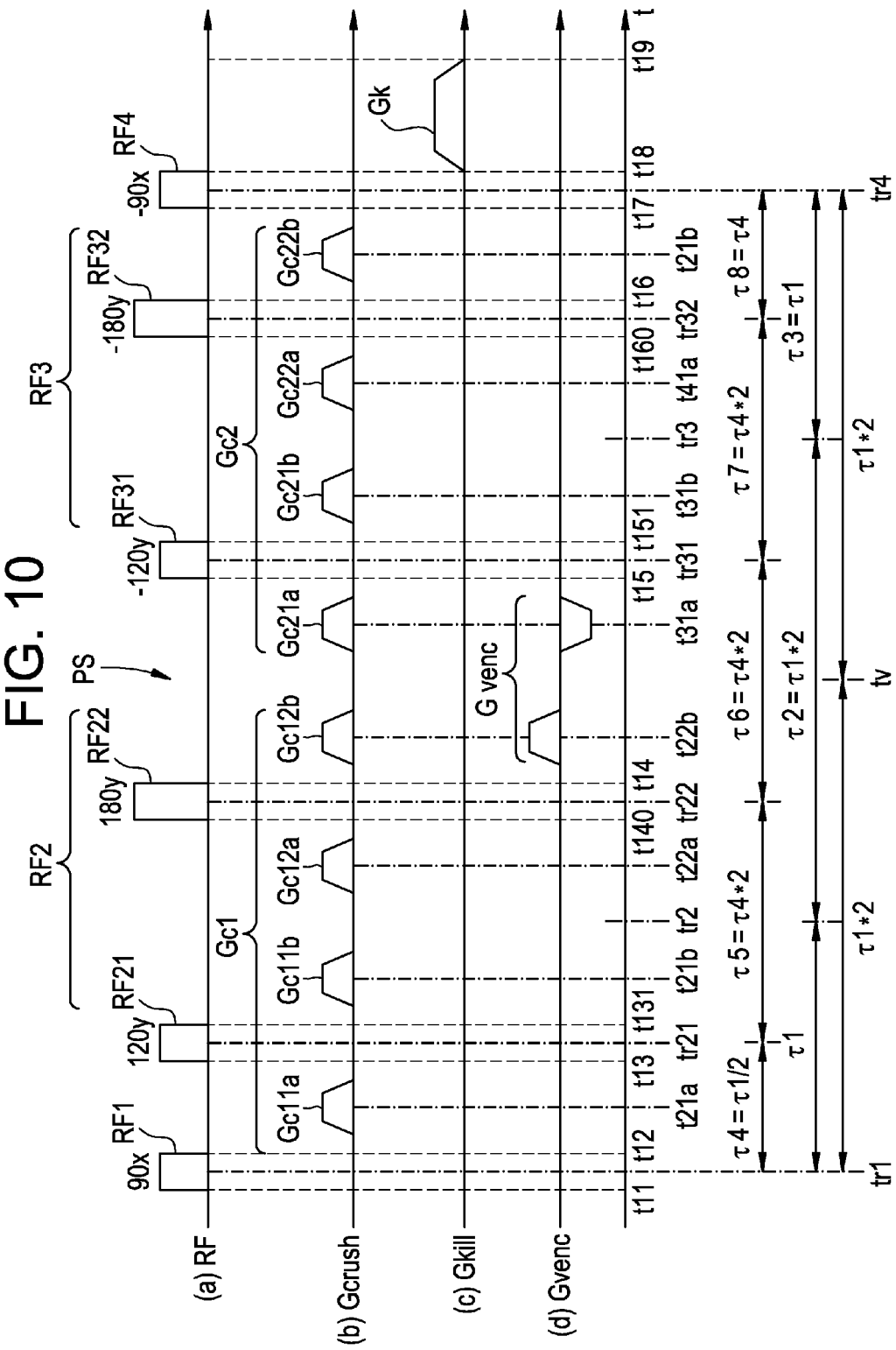
FIGS. 10(a), 10(b), 10(c), and 10(d) are pulse sequence diagrams showing a preparation sequence PS in a fourth embodiment according to the invention.

FIG. 10 is a pulse sequence diagram showing a preparation sequence PS in the fourth embodiment according to the invention.

In FIG. 10, (a) indicates a time base on which RF pulses RF are transmitted, (b) indicates a time base on which crusher gradient pulses Gcrush are transmitted as gradient pulses, (c) indicates a time base on which killer gradient pulses Gkill are transmitted as gradient pulses, and (d) indicates a time base on which each of velocity encode gradient pulses Gvenc is transmitted as a gradient pulse. At the respective (a), (b), (c) and (d), the horizontal axis indicates a time t, and the vertical axis indicates a pulse intensity, respectively. Here, Gcrush, Gkill and Gvenc are respectively at least one axial direction of a slice selection direction, a phase encode direction and a frequency encode direction.

As shown in FIG. 10, the present embodiment is different from the third embodiment and transmits the velocity encode gradient pulse Gvenc in the preparation sequence PS executed upon photographing a subject SU. The present embodiment is similar to the third embodiment except for this point. Therefore, explanation of dual portions or points will be omitted.

The scan section 2 transmits the velocity encode gradient pulse Gvenc as a preparation pulse thereby to shift the phases of spins moved in the subject according to the velocities thereof such that the phases thereof differ from one another. That is, the velocity encode gradient pulse is transmitted as the preparation pulse in such a manner that the phase of each spin held in a stationary state, having a first velocity corresponding to a velocity of 0, and the phase of each spin held in a moving state, which is moved at a second velocity different from the first velocity, are shifted from each other.

Here, the velocity encode gradient pulse Gvenc is transmitted in such a manner that it assumes a pair of gradient pulses opposite to each other in polarity on a time base t about a central point of time tv at which the velocity encode gradient pulse Gvenc is transmitted.

In the present embodiment as described above, the velocity encode gradient pulse Gvenc is transmitted. Therefore, the phases of the spins moved in the subject can be shifted according to the velocities thereof such that they differ from one another. Thus, the present embodiment is capable of more effectively obtaining images in which portions each moved at a predetermined moving velocity in the subject SU are emphasized. That is, flow voids can be generated in a multi-axial direction and flow spoiling having a quantitative property can be performed.

Thus, the present embodiment is capable of enhancing general versatility without using a contrast agent and improving image quality in a manner similar to the third embodiment.

Fifth embodiment. A fifth embodiment according to the invention will be explained below.

In the present embodiment, the scan section 2 obtains or acquires, as first imaging data, each magnetic resonance signal generated by executing an imaging sequence IS after a first preparation pulse sequence PS1 has been carried out as a preparation sequence PS. Along with it, the scan section 2 obtains, as second imaging data, each magnetic resonance signal generated by executing the imaging sequence IS after execution of a second preparation pulse sequence PS2 for transmitting preparation pulses identical to those for the first preparation pulse sequence PS1, except that no crusher gradient pulses Gc1 and Gc2 and velocity encode gradient pulse Gvenc are transmitted and the flip angles of the second RF pulse RF2 and the third RF pulse RF3 are different from each other.

The image generator 31 generates a first image, based on the first imaging data. The image generator 31 generates a second image, based on the second imaging data. Thereafter, a difference image produced by discriminating between the generated first and second images is assumed to be a subject's image.

The present embodiment is similar to the fourth embodiment except for the above. Therefore, explanation of dual portions will be omitted.

Figure 11:
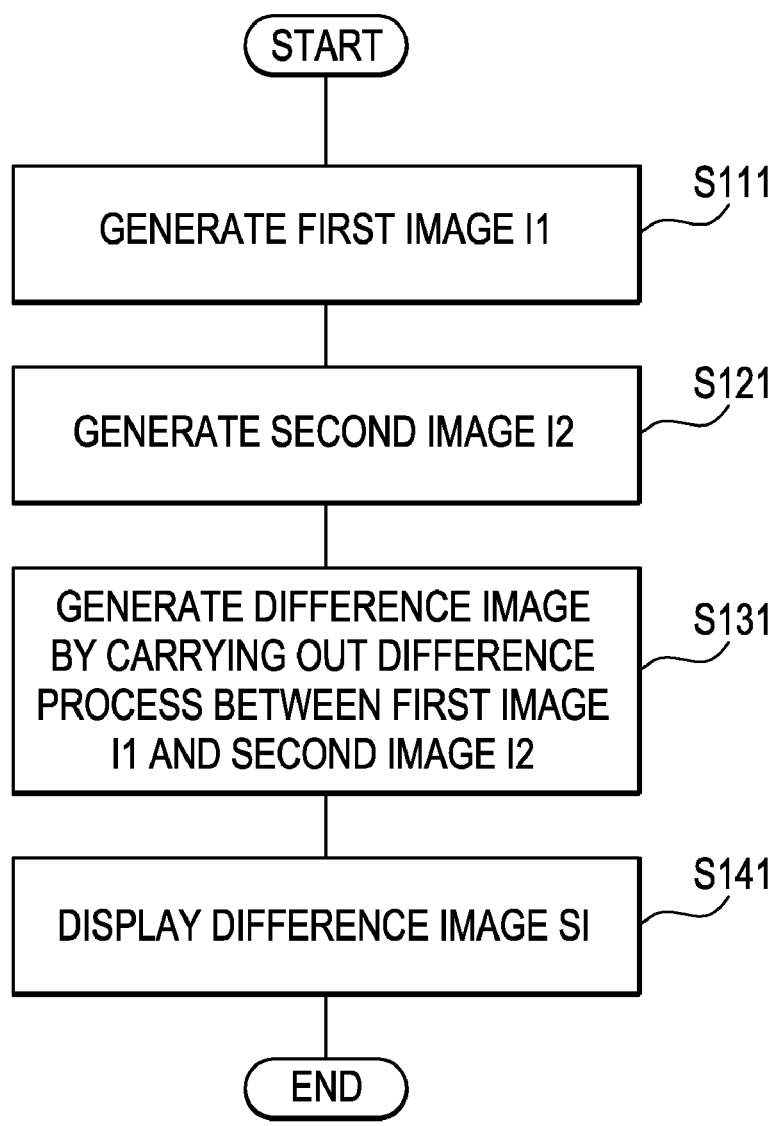
FIG. 11 is a flowchart illustrating operation of a fifth embodiment according to the invention at the time that a subject SU is photographed.

FIG. 11 is a flowchart illustrating operation of the fifth embodiment according to the invention at the time that a subject SU is photographed.

As shown in FIG. 11, a first image of the subject is generated (S111).

Figure 12:
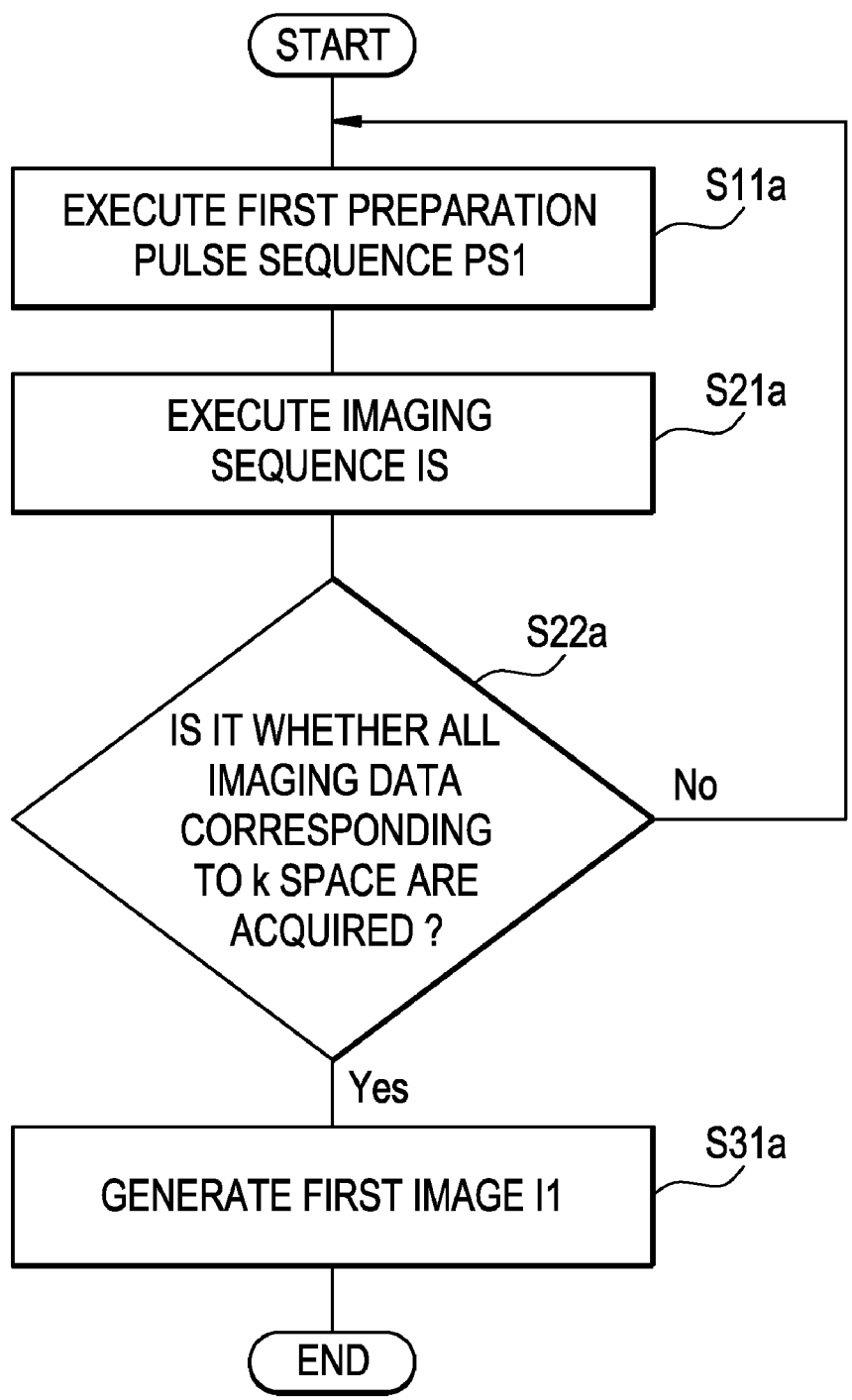
FIG. 12 is a flowchart showing the operation of generating a first image about the subject in the fifth embodiment according to the invention.

FIG. 12 is a flowchart showing the operation of generating the first image of the subject in the fifth embodiment according to the invention.

As shown in FIG. 12, the execution of the first preparation pulse sequence PS1 is first done (S11a).

Here, the scan section 2 executes the first preparation pulse sequence PS1.

Figure 13:
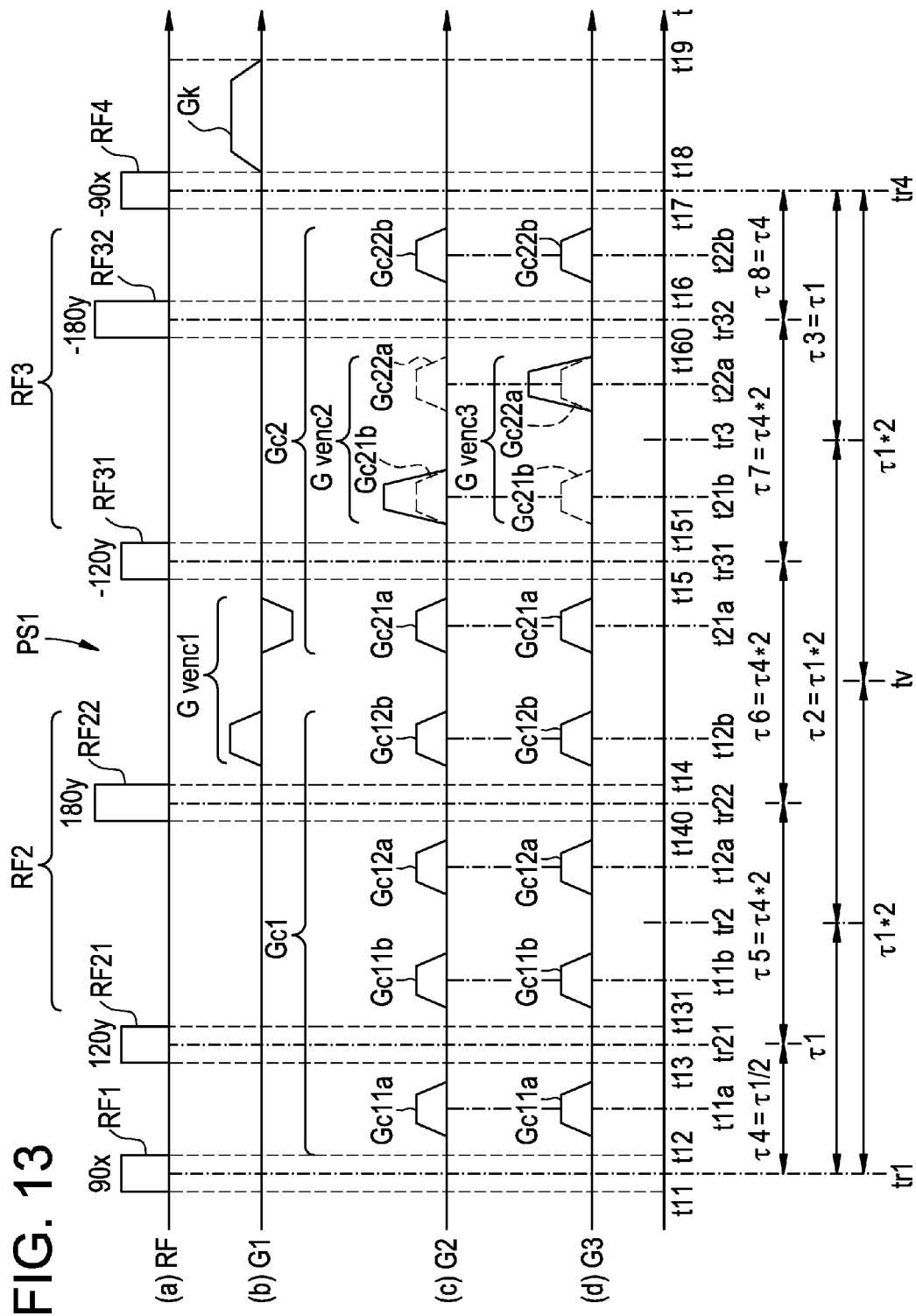
FIGS. 13(a), 13(b), 13(c), and 13(d) are pulse sequence diagrams illustrating a first preparation pulse sequence PS1 in the fifth embodiment according to the invention.

FIG. 13 is a pulse sequence diagram illustrating the first preparation pulse sequence PS1 in the fifth embodiment according to the invention.

In FIG. 13, (a) indicates a time base RF on which RF pulses are transmitted, and (b), (c) and (d) respectively indicate time bases in plural axial directions G1, G2 and G3 in which gradient pulses are transmitted. The horizontal axis indicates a time t, and the vertical axis indicates a pulse intensity, respectively. Here, each of G1, G2 and G3 indicates an axial direction that is an axial direction in which the gradient pulse is transmitted, and corresponds to any of a slice selection direction, a phase encode direction and a frequency encode direction.

In the present embodiment as shown in FIGS. 13(a), 13(b), 13(c) and 13(d), the first crusher gradient pulse Gc1 and the second crusher gradient pulse Gc2 are transmitted in the plural axial directions G2 and G3 unlike the preparation sequence PS executed in the fourth embodiment. Further, the velocity encode gradient pulses Gvenc are transmitted in the plural axial directions G1, G2 and G3. Except for this point, the preparation pulse sequence of the present embodiment is similar to the preparation sequence PS executed in the fourth embodiment.

In the present embodiment, as shown in FIGS. 13(b), 13(c) and 13(d), a first velocity encode gradient pulse Gvenc1, a second velocity encode gradient pulse Gvenc2 and a third velocity encode gradient pulse Gvenc3 are respectively transmitted in the three axial directions G1, G2 and G3 as the velocity encode gradient pulses Gvenc in a manner similar to the fourth embodiment. Here, the first velocity encode gradient pulse Gvenc1 is transmitted corresponding to a sixth time interval τ6 as viewed in the first axial direction G1. The second velocity encode gradient pulse Gvenc2 is transmitted corresponding to a seventh time interval τ7 as viewed in the second axial direction G2. The third velocity encode gradient pulse Gvenc3 is transmitted corresponding to the seventh time interval τ7 as viewed in the third axial direction G3.

As shown in FIGS. 13(c) and 13(d), the first crusher gradient pulse Gc1 and the second crusher gradient pulse Gc2 are transmitted in the two axial directions of the second and third axial directions G2 and G3 of the three axial directions G1, G2 and G3 in a manner similar to the fourth embodiment.

Here, as shown in FIGS. 13(c) and 13(d), the second velocity encode gradient pulse Gvenc2 and the third velocity encode gradient pulse Gvenc3 are transmitted during the seventh time interval τ7 at which a second α° pulse RF31 and a second 180° pulse RF32 are transmitted as a third RF pulse RF3. Therefore, the transmission of the gradient pulses Gc21b and Gc22a transmitted as the second crusher gradient pulse Gc2, and the transmission of the second and third velocity encode gradient pulses Gvenc2 and Gvenc3 overlap each other during the seventh time interval τ7. Therefore, as shown in FIGS. 13(c) and 13(d), the gradient pulses Gc21b and Gc22a transmitted as the second crusher gradient pulse Gc2 during the seventh time interval τ7 are indicated by dotted lines. The shape of each pulse obtained by adding both gradient pulses is indicated by a solid line.

After the execution of the first preparation pulse sequence PS1, the signal intensities by spins are obtained so as to differ depending on the velocities of the spins each moved within a subject as viewed in the plural axial directions G2 and G3 in a manner similar to the fourth embodiment.

As shown in FIG. 12, the imaging sequence IS is executed (S21a).

Here, the scan section 2 executes the imaging sequence IS by the SSFP type imaging method in a manner similar to the fourth embodiment.

Next, it is determined whether all imaging data corresponding to k space are acquired as shown in FIG. 12 (S22a).

Here, the controller 30 determines whether all imaging data corresponding to the k space are acquired, in a manner similar to the fourth embodiment. In the present embodiment, the imaging data are acquired or collected as the first imaging data. When it is determined that all the imaging data corresponding to the k space are not acquired (No), the execution (S11 a) of the preparation sequence PS and the execution (S21a) of the imaging sequence IS are sequentially done again as shown in FIG. 12.

On the other hand, when it is found that all the imaging data have been collected so as to correspond to the k space (Yes), a first image I1 is produced as shown in FIG. 12 (S31a).

Here, in a manner similar to the fourth embodiment, the scan section 2 sets the first imaging data obtained as the imaging data by its execution of the imaging sequence IS as raw data, and the image generator 31 reconstructs an image about the subject SU as the first image I1.

Next, a second image of the subject is produced as shown in FIG. 11 (S121).

Figure 14:
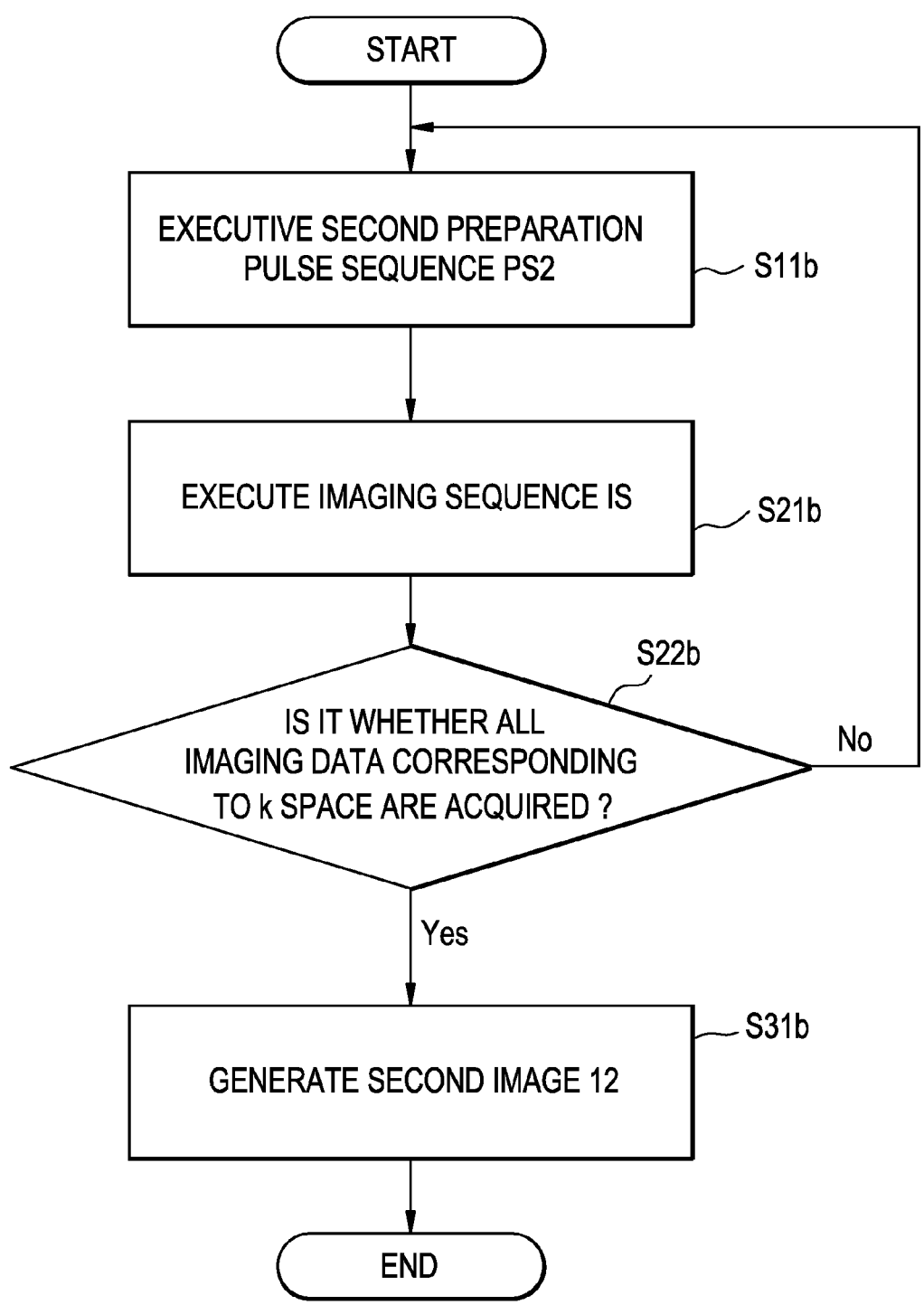
FIG. 14 is a flowchart depicting the operation of generating a second image about the subject in the fifth embodiment according to the invention.

FIG. 14 is a flowchart showing the operation of generating the second image of the subject in the fifth embodiment according to the invention.

As shown in FIG. 14, the second preparation pulse sequence PS2 is first executed (S11b).

Here, the scan section 2 executes the second preparation pulse sequence PS2.

Figure 15:
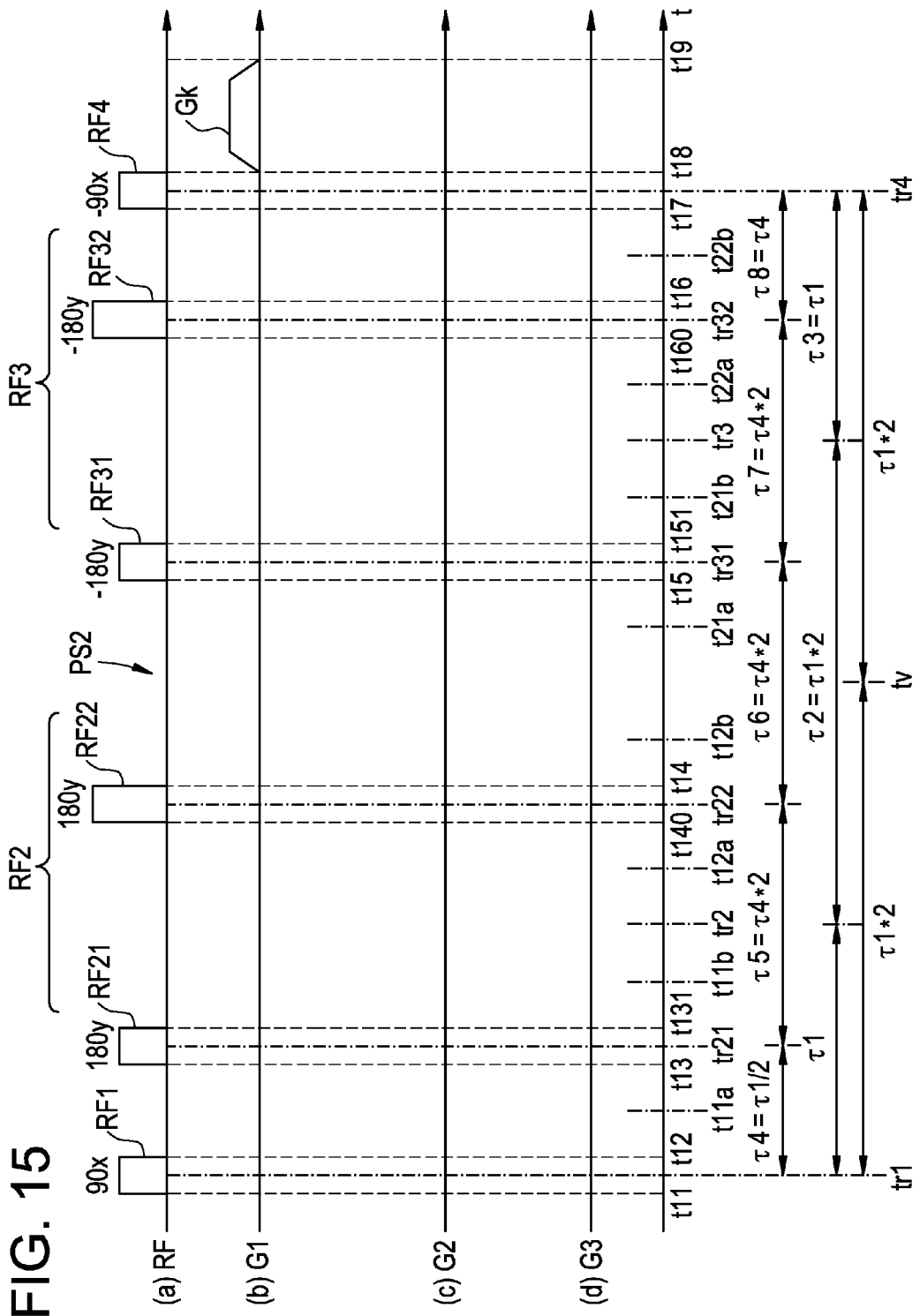
FIGS. 15(a), 15(b), 15(c), and 15(d) are pulse sequence diagrams showing a second preparation pulse sequence PS2 in the fifth embodiment according to the invention.

FIG. 15 is a pulse sequence diagram showing the second preparation pulse sequence PS2 in the fifth embodiment according to the invention.

In FIG. 15, (a) indicates a time base RF on which RF pulses are transmitted, and (b), (c) and (d) respectively indicate time bases in plural axial directions G1, G2 and G3 in which gradient pulses are transmitted. The horizontal axis indicates a time t, and the vertical axis indicates a pulse intensity, respectively. Here, each of G1, G2 and G3 indicates an axial direction that is an axial direction in which the gradient pulse is transmitted, and corresponds to any of a slice selection direction, a phase encode direction and a frequency encode direction.

As shown in FIGS. 15(a), 15(b), 15(c) and 15(d), the second preparation pulse sequence PS2 is different from the first preparation pulse sequence PS1 referred to above, and no crusher gradient pulses Gc1 and Gc2 and velocity encode gradient pulses Gvenc are transmitted. The flip angles of the second RF pulse RF2 and the third RF pulse RF3 are different from each other. Except for this point, the second preparation pulse sequence PS2 is similar to the first preparation pulse sequence PS1.

In the present embodiment, the absolute values of flip angles of a first α° pulse RF21 and a second α° pulse RF31 are set as 180° unlike the first preparation pulse sequence PS1. That is, the first α° pulse RF21 is transmitted as a 180° y pulse, and the second α° pulse RF31 is transmitted as a −180° y pulse.

As shown in FIGS. 15(b), 15(c) and 15(d), the first velocity encode gradient pulse Gvenc1, second velocity encode gradient pulse Gvenc2 and third velocity encode gradient pulse Gvenc3 are not transmitted unlike the first preparation pulse sequence PS1. As shown in FIGS. 15(c) and 15(d), no first and second crusher gradient pulses Gc1 and Gc2 are transmitted.

After execution of the second preparation pulse sequence PS2, the signal intensity by each spin is obtained so as not to vary depending upon the velocity of each spin moved within the subject unlike the first preparation pulse sequence PS1.

Next, the imaging sequence IS is executed as shown in FIG. 14 in the same manner as when the first image I1 is produced (S21b). It is determined in the same manner as when the first image I1 is produced, whether all imaging data corresponding to k space are acquired (S22b). When it is determined that all the imaging data are acquired so as to correspond to the k space (Yes), a second image I2 is produced (S31b).

Next, as shown in FIG. 11, a difference image SI is produced by discriminating between the first image I1 and the second image I2 (S131).

Here, the image generator 31 carries out a difference process between the first image I1 and the second image I2 produced with respect to the same slice surface at the subject in the above-described manner and generates the difference image, based on the value in difference therebetween. For instance, the process of discriminating between pixel values of pixels at positions where they correspond to each other at the first image I1 and the second image I2 to thereby calculate a difference value is executed for each pixel. Then, the difference values obtained every pixel are disposed at their corresponding pixel positions to thereby produce a difference image SI. Incidentally, the images are subjected to the difference process while leaving them unchanged as complex data, whereby the difference image SI may be produced.

Next, the difference image SI is displayed as shown in FIG. 11 (S141).

Here, the display unit 33 receives data about the difference image SI produced as described above, from the image generator 31 and displays the difference image on its display screen.

In the present embodiment as described above, each magnetic resonance signal produced by executing the imaging sequence after the first preparation pulse sequence PS1 corresponding to the preparation pulse sequence PS of the fourth embodiment has been carried out is acquired as the first imaging data. Each magnetic resonance signal produced by executing the imaging sequence after execution of the second preparation pulse sequence PS2 for transmitting the same preparation pulses as those for the first preparation pulse sequence PS1, except that no crusher gradient pulses Gc1 and Gc2 and velocity encode gradient pulses Gvenc are transmitted and the flip angles of the second RF pulse RF2 and the third RF pulse RF3 are different from each other, is obtained as the second imaging data. The first image is generated based on the first imaging data, and the second image is generated based on the second imaging data. Thereafter, the difference image is produced by carrying out the difference process between the first and second images.

In the present embodiment, the first image I1 can be produced as an image in which the signal intensity from each spin held in the moving state is suppressed with respect to each spin held in the stationary state, in a manner similar to the fourth embodiment. That is, the first image results in an image in which the flow of blood or the like flowing through the subject is suppressed. On the other hand, the second image I2 is produced as an image in which the signal intensity from each spin held in the moving state is not suppressed, in a manner similar to the fourth embodiment. That is, the second image results in a flow suppression-free image. Therefore, the difference image SI produced by carrying out the difference process between the first image I1 and the second image I2 results in a flow-emphasized MRA image because the signal intensity from each spin held in the moving state corresponds to the difference value. Since the second preparation pulse sequence PS2 is executed as the preparation sequence even upon generation of the second image I2 in the present embodiment in particular, contrast can be prevented from varying. Further, since a signal from a flow of an artery or the like is 180° rotated by the corresponding velocity encode gradient pulse Gvenc and may have a negative value, the absolute value of a signal corresponding to the flow at the difference image SI becomes larger than the first image I1, and the an S/N ratio can hence be enhanced. Therefore, emphasis on the flow is displayed with high accuracy at the difference image SI.

The amount of the signal to be attenuated by execution of the first preparation pulse sequence PS1 referred to above can easily be calculated from the area (time integration value) of each of the gradient pulses such as the crusher gradient pulses Gc1 and Gc2 and the velocity encode gradient pulses Gvenc. Therefore, an image in which a necessary flow is emphasized suitably, can easily be produced by measuring the moving velocity of the flow using the phase contrast method or the like, for example.

Since no gradient pulses are transmitted in the second preparation pulse sequence PS2, a flow running in the slice selection direction can also be represented or projected with ease. Since the gradient pulses such as the crusher gradient pulses Gc1 and Gc2 and the velocity encode gradient pulses Gvenc can be transmitted in the plural axial directions in the first preparation pulse sequence PS1, flows running in the respective axial directions can be all projected or represented.

Thus, the present embodiment is capable of enhancing general versatility without using a contrast agent and improving image quality.

Sixth embodiment. A sixth embodiment according to the invention will be explained below.

Figure 16:
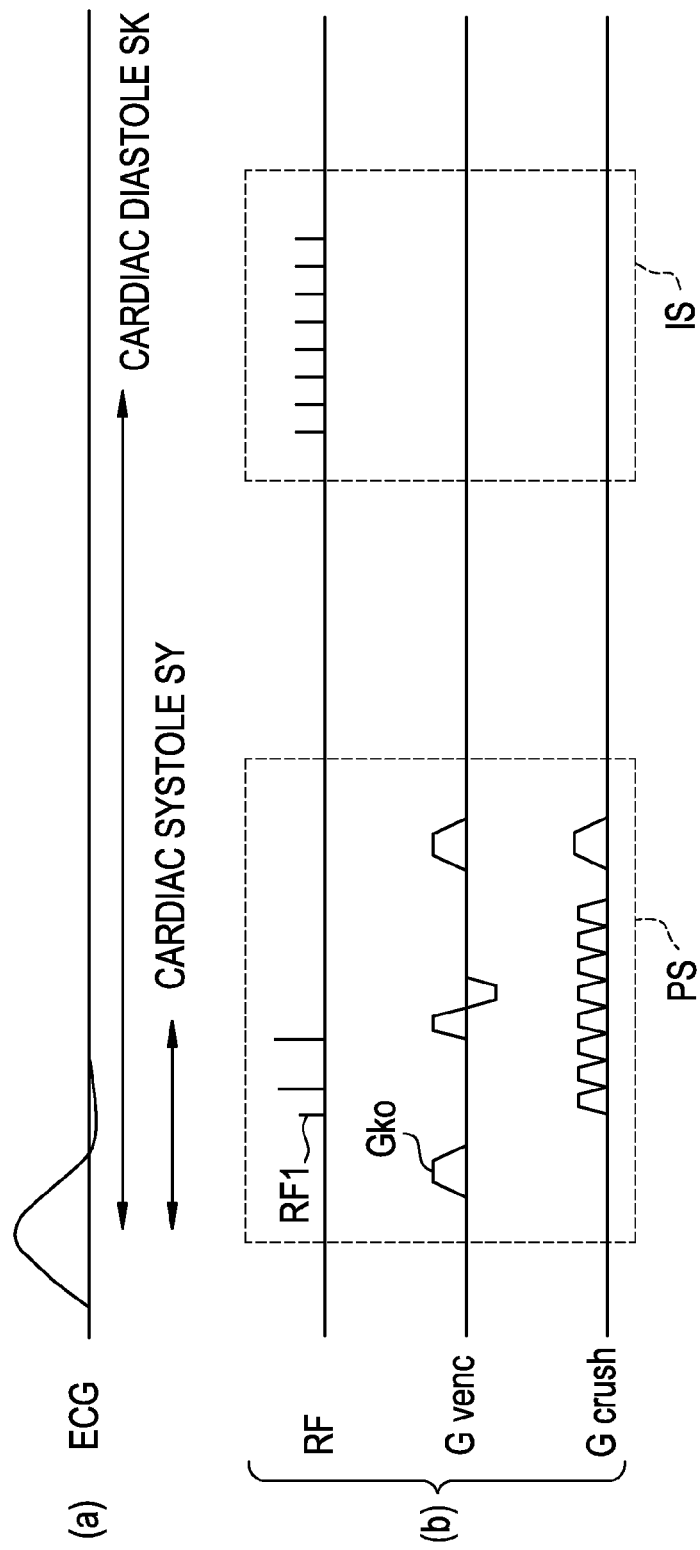
FIGS. 16(a) and 16(b) are diagrams illustrating the manner in which a preparation sequence PS and an imaging sequence IS are executed in a sixth embodiment according to the invention.

FIG. 16 is a diagram illustrating the manner in which a preparation sequence PS and an imaging sequence IS are executed in the sixth embodiment according to the invention. In FIG. 16, the horizontal axis indicates a time base t, (a) indicates transition of a cardiac signal ECG of a subject, and (b) indicates that the timing provided for each of pulses transmitted upon execution of the preparation sequence PS and the imaging sequence IS is associated with the cardiac signal ECG of the subject.

As shown in FIG. 16, the present embodiment specifies timing provided to execute each of the preparation sequence PS and the imaging sequence IS. As a preparation pulse in the preparation sequence PS, a killer gradient pulse Gk0 is transmitted to the subject before transmission of a first RF pulse RF1 in such a manner that a gradient magnetic field for causing transverse magnetization of each spin to disappear is produced. The present embodiment is similar to the fourth embodiment except for this point. Therefore, explanation of dual portions will be omitted.

In the present embodiment, as shown in FIG. 16, the scan section 2 executes the preparation sequence PS so as to correspond to cardiac systole SY at cardiac motion of the subject and thereafter performs the imaging sequence IS so as to correspond to cardiac diastole SK at its cardiac motion.

Described specifically, the flow rate of a flow such as blood flowing through the subject is first measured by using a cardiac-synchronized phase contrast method. Then, the timings provided for the cardiac systole SY and the cardiac diastole SK at the cardiac motion of the subject are specified. Thereafter, the preparation sequence PS and the imaging sequence IS are respectively executed so as to correspond to the specified timings as shown in FIG. 16.

Thus, the present embodiment is capable of easily distinguishing between the blood and other stationary portion to carry out the preparation sequence PS during cardiac systole in which the moving velocity of blood is in an increased state under the cardiac motion of the subject. The occurrence of body-motion artifacts or the like in each imaged pictorial image is suppressed to execute the imaging sequence IS during cardiac diastole in which the moving velocity of blood is in a decreased state. Further, since the time at which the flow is slow is a long time of a few 100 msecs during cardiac diastole, imaging data can be acquired sufficiently. Since the transverse magnetization of each spin disappears by the killer gradient pulse Gk0 before transmission of the first RF pulse RF1 in the present embodiment, image quality can further be improved.

Incidentally, the magnetic resonance imaging apparatus 1 of the above embodiment is equivalent to the magnetic resonance imaging apparatus of the invention. The scan section 2 of the above embodiment corresponds to the scan section of the invention. The image generator 31 of the above embodiment corresponds to the image generator of the invention. The display unit 33 of the above embodiment corresponds to the display unit of the invention.

Upon implementation of the invention, the invention is not limited to the above-described embodiments, and various modifications can be adopted.

Upon transmitting the RF pulses as the preparation pulses, for example, the invention is not limited to the above-described values of flip angles. In the case, a slice selection may be performed. Fat suppression methods such as a CHESS (Chemical Shift Selectivity) method, a Spectral IR method and the like may be used in combination. T2 contrast may be controlled by adjusting the time between the first RF pulse RF1 and the fourth RF pulse RF4.

Although the above embodiment has explained the case in which the rectangular pulses wide in frequency and effective in nonuniformity of the static magnetic field are transmitted as the RF pulses, the invention is not limited to it.

Upon transmitting the velocity encode gradient pulse as the preparation pulse, for example, it may be transmitted to a plurality of arbitrary axes. The velocity encode gradient pulse may be transmitted in an arbitrary area or may be transmitted in accordance with the arbitrary number of times in addition to it.

For instance, the imaging sequence may be executed by various techniques such as FSE (Fast Spin Echo), SE (Spin Echo), GRE (Gradient Recalled Echo), SPGR (Spoiled GRASS) and the like in addition to the SSFP method. It is preferable if the invention is applied to three-dimensional imaging in particular.

For example, the flip angles, phases and transmission timings of the first RF pulse RF1, second RF pulse RF2, third RF pulse RF3 and fourth RF pulse RF4 can arbitrarily be set.

The invention may be applied to a case in which the above scan is executed in sync with respiratory movements of a subject. Here, it is preferable to execute a scan in sync with the state of expiration or inspiration, for example.

The invention may be applied even to a case in which the signal intensity of magnetization at a specific flow rate is attenuated and the signal intensity of magnetization other than it is maintained, in addition to the case in which the signal intensity of each spin moved at the specific flow rate by magnetization is attenuated and the signal intensity of each spin held in the stationary state by magnetization is maintained.

Many widely different embodiments of the invention may be configured without departing from the spirit and the scope of the present invention. It should be understood that the present invention is not limited to the specific embodiments described in the specification, except as defined in the appended claims.

The invention claimed is:

1. A magnetic resonance imaging apparatus which executes an imaging sequence for obtaining, as imaging data, magnetic resonance signals generated from a spin excited at a subject within a static magnetic field space, and produces an image of the subject based on the imaging data obtained by the execution of the imaging sequence, said apparatus comprising:
   a scan section which executes the imaging sequence and executes, before the execution of the imaging sequence, a preparation sequence for transmitting preparation pulses to the subject in such a manner that signal intensities of the magnetic resonance signals differ according to the velocities of spins moved in the subject,
   wherein the scan section sequentially transmits, as the preparation pulses, a first RF pulse, a second RF pulse, a third RF pulse and a fourth RF pulse respectively to the subject,
   wherein the scan section transmits a first crusher gradient pulse constituted of a pair of gradient pulses to the subject in such a manner that a point of time at which an RF pulse is transmitted as the second RF pulse is interposed at a time base,
   wherein the scan section transmits a second crusher gradient pulse constituted of a pair of gradient pulses to the subject in such a manner that a point of time at which an RF pulse is transmitted as the third RF pulse is interposed at the time base, and
   wherein the scan section transmits a killer gradient pulse to the subject after the transmission of the fourth RF pulse.

2. The magnetic resonance imaging apparatus according to claim 1, wherein the scan section transmits the first RF pulse and the fourth RF pulse in such a manner that the phases of the first RF pulse and the fourth RF pulse are the same, the absolute values of the flip angles of the first RF pulse and the fourth RF pulse are the same, and the signs of the first RF pulse and the fourth RF pulse are opposite to each other.

3. The magnetic resonance imaging apparatus according to claim 1, wherein the scan section transmits the first RF pulse and the fourth RF pulse in such a manner that the absolute values of the flip angles of the first RF pulse and the fourth RF pulse assume 90°.

4. The magnetic resonance imaging apparatus according to claim 2, wherein the scan section transmits the first RF pulse and the fourth RF pulse in such a manner that the absolute values of the flip angles of the first RF pulse and the fourth RF pulse assume 90°.

5. The magnetic resonance imaging apparatus according to claim 3, wherein the scan section transmits the second RF pulse and the third RF pulse in such a manner that the phases of the second RF pulse and the third RF pulse are orthogonal to the phases of the first RF pulse and the fourth RF pulse.

6. The magnetic resonance imaging apparatus according to claim 4, wherein the scan section transmits the second RF pulse and the third RF pulse in such a manner that the phases the second RF pulse and the third RF pulse are orthogonal to the phases of the first RF pulse and the fourth RF pulse.

7. The magnetic resonance imaging apparatus according to claim 5, wherein the scan section transmits the second RF pulse and the third RF pulse in such a manner that the absolute values of the flip angles of the second RF pulse and the third RF pulse are identical to each other.

8. The magnetic resonance imaging apparatus according to claim 6, wherein the scan section transmits the second RF pulse and the third RF pulse in such a manner that the absolute values of the flip angles of the second RF pulse and the third RF pulse are identical to each other.

9. The magnetic resonance imaging apparatus according to claim 1, wherein the scan section sequentially transmits the first RF pulse, the second RF pulse, the third RF pulse and the fourth RF pulse, respectively, to the subject in such a manner that a second time interval defined between a central point of time at which the second RF pulse is transmitted, and a central point of time at which the third RF pulse is transmitted, is twice as much as a first time interval defined between a central point of time at which the first RF pulse is transmitted and a central point of time at which the second RF pulse is transmitted, and a third time interval defined between a central point of time at which the third RF pulse is transmitted and a central point of time at which the fourth RF pulse is transmitted, is identical to the first time interval.

10. The magnetic resonance imaging apparatus according to claim 2, wherein the scan section sequentially transmits the first RF pulse, the second RF pulse, the third RF pulse and the fourth RF pulse, respectively, to the subject in such a manner that a second time interval defined between a central point of time at which the second RF pulse is transmitted, and a central point of time at which the third RF pulse is transmitted, is twice as much as a first time interval defined between a central point of time at which the first RF pulse is transmitted and a central point of time at which the second RF pulse is transmitted, and a third time interval defined between a central point of time at which the third RF pulse is transmitted and a central point of time at which the fourth RF pulse is transmitted, is identical to the first time interval.

11. The magnetic resonance imaging apparatus according to claim 1, wherein the scan section transmits a plurality of RF pulses including a 180° pulse as the second RF pulse, and transmits a plurality of RF pulses including the 180° pulse as the third RF pulse.

12. The magnetic resonance imaging apparatus according to claim 11, wherein the scan section transmits the RF pulses respectively transmitted as the second RF pulse and the third RF pulse in such a manner that the phases of the second RF pulse and the third RF pulse are the same, the absolute values of the flip angles of the second RF pulse and the third RF pulse are the same and the signs of the second RF pulse and the third RF pulse are opposite to each other.

13. The magnetic resonance imaging apparatus according to claim 12, wherein the scan section sequentially transmits pulses other than the 180° pulse as the second RF pulse, and 180° pulses as the third RF pulse.

14. The magnetic resonance imaging apparatus according to claim 1, wherein the scan section transmits the first crusher gradient pulse and the second crusher gradient pulse, respectively, in such a manner that a gradient pulse transmitted between the first RF pulse and the second RF pulse and a gradient pulse transmitted between the third RF pulse and the fourth RF pulse, of a plurality of gradient pulses respectively transmitted as the first crusher gradient pulse and the second crusher gradient pulse, are respectively set to the same first time integration value with respect to each other, and the whole time integration value of gradient pulses respectively transmitted as the second RF pulse and the third RF pulse between a plurality of RF pulses is set to a second time integration value equal to twice the first time integration value.

15. The magnetic resonance imaging apparatus according to claim 1, wherein the scan section transmits, as the preparation pulses, velocity encode gradient pulses for shifting the phases of moving spins in a different way according to the velocities of the moving spins in the spins of the subject.

16. The magnetic resonance imaging apparatus according to claim 15, wherein the scan section transmits the velocity encode gradient pulses such that the pulses are opposite to each other in polarity at the time base about central points of time at which the velocity encode gradient pulses are transmitted.

17. The magnetic resonance imaging apparatus according to claim 15, further including an image generation unit which produces an image of the subject, based on the imaging data, wherein the scan section acquires a magnetic resonance signal produced by executing the imaging sequence after the preparation sequence has been executed as a first preparation pulse sequence, as first imaging data, wherein the scan section acquires, as second imaging data, a magnetic resonance signal produced by executing the imaging sequence after a second preparation pulse sequence for transmitting the same preparation pulses as in the first preparation sequence is executed as the preparation sequence, except that the crusher gradient pulses and the velocity encode gradient pulse are not transmitted and the flip angles of the second RF pulse and the third RF pulse are different from each other, and wherein the image generation unit generates a first image, based on the first imaging data and generates a second image, based on the second imaging data, and thereafter generates, as the image, a difference image by carrying out a difference process between the first and second images.

18. The magnetic resonance imaging apparatus according to claim 1, wherein the scan section transmits, as the preparation pulse, a killer gradient pulse for generating a gradient magnetic field that causes transverse magnetization of each spin to disappear at the subject, before the transmission of the first RF pulse.

19. The magnetic resonance imaging apparatus according to claim 1, wherein the scan section transmits the first RF pulse, the second RF pulse, the third RF pulse and the fourth RF pulse as rectangular pulses.

20. The magnetic resonance imaging apparatus according to claim 1, wherein the scan section performs the preparation sequence during cardiac systole at cardiac motion of the subject, and performs the imaging sequence during cardiac diastole at the cardiac motion.

* * * * *